United States Patent
Yorikado et al.

(10) Patent No.: US 12,356,735 B2
(45) Date of Patent: Jul. 8, 2025

(54) LIGHT RECEIVING ELEMENT AND LIGHT RECEIVING APPARATUS

(71) Applicant: SONY SEMICONDUCTOR SOLUTIONS CORPORATION, Kanagawa (JP)

(72) Inventors: Yuhi Yorikado, Kanagawa (JP); Yoshiki Ebiko, Kanagawa (JP); Suzunori Endo, Kanagawa (JP); Nobuhiro Kawai, Kanagawa (JP); Fumihiko Koga, Kanagawa (JP); Nobuo Nakamura, Kanagawa (JP); Sozo Yokogawa, Kanagawa (JP); Hayato Wakabayashi, Tokyo (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 341 days.

(21) Appl. No.: 17/781,666

(22) PCT Filed: Dec. 3, 2020

(86) PCT No.: PCT/JP2020/044962
§ 371 (c)(1),
(2) Date: Jun. 1, 2022

(87) PCT Pub. No.: WO2021/117589
PCT Pub. Date: Jun. 17, 2021

(65) Prior Publication Data
US 2022/0375969 A1  Nov. 24, 2022

(30) Foreign Application Priority Data

Dec. 13, 2019 (JP) .................................. 2019-225912
Oct. 1, 2020 (JP) .................................. 2020-166859

(51) Int. Cl.
*H10F 39/10* (2025.01)
*G01S 7/481* (2006.01)
*G01S 7/4863* (2020.01)

(52) U.S. Cl.
CPC .......... *H10F 39/103* (2025.01); *G01S 7/4811* (2013.01); *G01S 7/4863* (2013.01); *H10F 39/107* (2025.01)

(58) Field of Classification Search
CPC ............ G01S 7/4863; H01L 27/14603; H01L 27/14614; H10F 39/107; H10F 39/807; H10F 39/199; H10F 39/8057; H10F 55/25
See application file for complete search history.

(56) References Cited

U.S. PATENT DOCUMENTS

2013/0200479 A1* 8/2013 Sakano ............. H01L 27/14641
257/443
2013/0214371 A1  8/2013 Asatsuma et al.
(Continued)

FOREIGN PATENT DOCUMENTS

CN  105229790 A  1/2016
CN  110383480 A  10/2019
(Continued)

OTHER PUBLICATIONS

International Search Report and Written Opinion prepared by the Japan Patent Office on Jan. 8, 2021, for International Application No. PCT/JP2020/044962, 3 pgs.

*Primary Examiner* — Thanh Luu
(74) *Attorney, Agent, or Firm* — Sheridan Ross PC

(57) ABSTRACT

To provide a light receiving element including: a photoelectric conversion unit (PD) that is provided in a semiconductor substrate and converts light into a charge; a first charge accumulation unit (MEM) to which the charge is transferred from the photoelectric conversion unit; a second charge
(Continued)

accumulation unit (MEM) to which the charge is transferred from the photoelectric conversion unit, in which each of the first and second charge accumulation units includes a stack of an electrode, a first insulating layer, and a semiconductor layer.

22 Claims, 27 Drawing Sheets

(56) References Cited

U.S. PATENT DOCUMENTS

| | | | |
|---|---|---|---|
| 2016/0276612 A1* | 9/2016 | Gotanda | H10K 30/83 |
| 2017/0045618 A1* | 2/2017 | Mase | H01L 31/12 |
| 2017/0332029 A1* | 11/2017 | Feick | G01S 17/894 |
| 2018/0156898 A1 | 6/2018 | Suzuki et al. | |
| 2018/0288343 A1 | 10/2018 | McCarten | |
| 2018/0366504 A1 | 12/2018 | Jin | |
| 2019/0096933 A1 | 3/2019 | Kido | |
| 2019/0281241 A1 | 9/2019 | Jin | |
| 2020/0035724 A1 | 1/2020 | Machida et al. | |
| 2020/0382736 A1* | 12/2020 | Na | H04N 25/705 |
| 2021/0066358 A1 | 3/2021 | Nakagawa | |

FOREIGN PATENT DOCUMENTS

| | | |
|---|---|---|
| EP | 2187237 A1 | 5/2010 |
| JP | 2011-054832 | 3/2011 |
| JP | 2012169530 A | 9/2012 |
| JP | 2013-207321 | 10/2013 |
| JP | 2018-147975 | 9/2018 |
| JP | 2019-004149 | 1/2019 |
| JP | 2019-145563 | 8/2019 |
| JP | 2019165066 A | 9/2019 |
| TW | I596747 B | 8/2017 |
| WO | WO 2017/022220 | 2/2017 |
| WO | WO 2019/181466 | 9/2019 |

* cited by examiner

LIGHT RECEIVING ELEMENT AND LIGHT RECEIVING APPARATUS

CROSS REFERENCE TO RELATED APPLICATIONS

This application is a national stage application under 35 U.S.C. 371 and claims the benefit of PCT Application No. PCT/JP2020/044962, having an international filing date of 3 Dec. 2020, which designated the United States, which PCT application claimed the benefit of Japanese Patent Application Nos. 2019-225912, filed 13 Dec. 2019, and 2020-166859, filed 1 Oct. 2020, the entire disclosures of each of which are incorporated herein by reference.

FIELD

The present disclosure relates to a light receiving element and a light receiving apparatus.

BACKGROUND

As a method for measuring a distance to an object, a time of flight (TOF) sensor (light receiving apparatus) is known. For example, in the case of an indirect TOF sensor, the TOF sensor can measure the distance to the object by irradiating the object with irradiation light having a predetermined cycle and detecting a phase difference between the irradiation light and the reflected light. Then, in the TOF sensor, by repeating light reception a plurality of times at short intervals, a signal amount is increased to increase a signal/noise (S/N) ratio, enabling highly accurate distance measurement.

CITATION LIST

Patent Literature

Patent Literature 1: Japanese Patent Application Laid-open No. 2019-4149

SUMMARY

Technical Problem

In order to perform distance measurement while ensuring a sufficient S/N ratio, a light receiving element of a TOF sensor (light receiving apparatus) is required to have a wide dynamic range, that is, to increase an amount of accumulated charges generated by light reception.

Furthermore, the light receiving element is required to reduce the influence of kTC noise for highly accurate distance measurement.

Therefore, in view of such a situation, the present disclosure proposes a light receiving element and a light receiving apparatus capable of reducing the influence of kTC noise while ensuring a wide dynamic range.

Solution to Problem

According to the present disclosure, a light receiving element is provided. The light receiving element includes: a photoelectric conversion unit that is provided in a semiconductor substrate and converts light into a charge; a first charge accumulation unit to which the charge is transferred from the photoelectric conversion unit; and a second charge accumulation unit to which the charge is transferred from the photoelectric conversion unit. In the light receiving element, each of the first and second charge accumulation units includes a stack of an electrode, a first insulating layer, and a semiconductor layer.

Also, according to the present disclosure, a light receiving element is provided. The light receiving element includes: a photoelectric conversion unit that is provided in a semiconductor substrate and converts light into a charge; a first charge accumulation unit to which the charge is transferred from the photoelectric conversion unit; and a second charge accumulation unit to which the charge is transferred from the photoelectric conversion unit. In the light receiving element, each of the first and second charge accumulation units includes: a semiconductor layer; an insulating layer embedded in a trench formed in the semiconductor layer; and a vertical electrode embedded in the insulating layer.

Moreover, according to the present disclosure, a light receiving apparatus is provided. The light receiving apparatus includes one or more light receiving elements. The light receiving element includes: a photoelectric conversion unit that is provided in a semiconductor substrate and converts light into a charge; a first charge accumulation unit to which the charge is transferred from the photoelectric conversion unit; and a second charge accumulation unit to which the charge is transferred from the photoelectric conversion unit. In the light receiving element, each of the first and second charge accumulation units includes a stack of an electrode, a first insulating layer, and a semiconductor layer.

DESCRIPTION OF EMBODIMENTS

Figure 1:
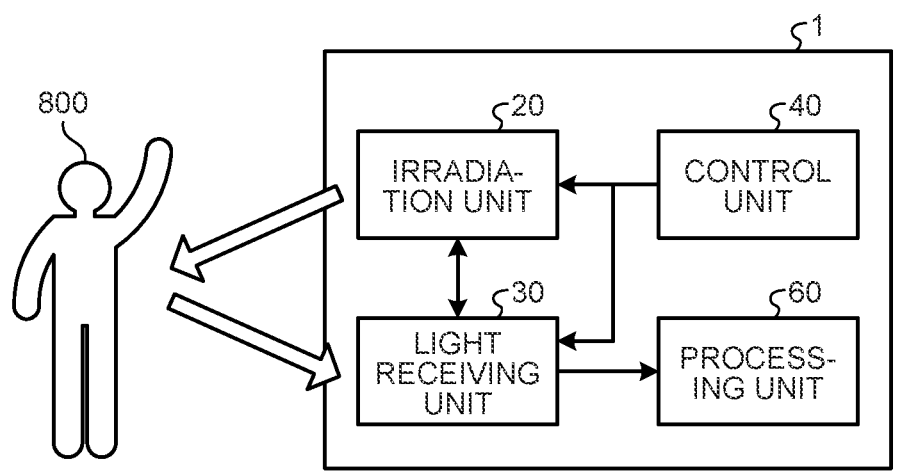
FIG. 1 is a block diagram illustrating a configuration example of a distance measurement module 1 according to an embodiment of the present disclosure.

Preferred embodiments of the present disclosure will be described in detail hereinbelow with reference to the accompanying drawings. Note that redundant descriptions will be omitted from the present specification and the drawings by assigning the same reference signs to components having substantially the same function configuration.

Further, in this specification and the drawings, a plurality of components having substantially the same or similar functional configuration may be distinguished by assigning the same reference numerals followed by different numbers in some cases. However, when it is unnecessary to particularly distinguish each of the plurality of components having substantially the same or similar functional configuration, only the same reference numeral is assigned. Further, similar components of different embodiments may be distinguished by assigning the same reference numerals followed by different alphabets in some cases. However, when it is unnecessary to particularly distinguish each of the similar components, only the same reference numeral is assigned.

Further, the drawings referred to in the following description are drawings for promoting the description of the embodiments of the present disclosure and the understanding thereof, and shapes, dimensions, ratios, and the like illustrated in the drawings may be different from actual ones for the sake of clarity. Furthermore, components and the like included in elements and apparatuses illustrated in the drawings can be appropriately changed in design in consideration of the following description and known techniques.

Further, in the following description, a case where the embodiments of the present disclosure are applied to a back-illuminated light receiving apparatus will be described as an example, and thus in the light receiving apparatus, light is incident from the back surface side of the substrate. Thus, in the following description, the front surface of the substrate is a surface facing the back surface when the light incident side is the back surface.

The description of specific lengths and shapes in the following description does not mean only the same values as mathematically defined numerical values or geometrically defined shapes. In detail, the description of specific lengths and shapes in the following description includes a case where there is an allowable difference (error/distortion) in the element, the manufacturing process thereof, and the use/operation thereof, and a shape similar to the shape. For example, in the following description, the expression "circular shape" or "substantially circular shape" means that the shape is not limited to a perfect circle but includes a shape similar to a perfect circle such as an elliptical shape.

Furthermore, in the following description of circuits (electrical connections), unless otherwise specified, "electrically connected" means that a plurality of elements is connected such that electricity (signals) conducts. In addition, "electrically connected" in the following description includes not only a case of directly and electrically connecting a plurality of elements but also a case of indirectly and electrically connecting a plurality of elements via other elements.

Further, in the following description, "sharing" means that other elements are provided so as to be shared by a plurality of one elements, in other words, the other elements are shared by a predetermined number of each of the one elements, unless otherwise specified.

Note that the description will be given in the following order.

1. Configuration example of the distance measurement module 1 according to the embodiment of the present disclosure
2. Configuration example of the light receiving unit 30 according to the embodiment of the present disclosure
3. Equivalent circuit of the light receiving element 10 according to the embodiment of the present disclosure
4. Principle of distance calculation method using the distance measurement module 1 according to the embodiment of the present disclosure
5. Background leading to creation of the present embodiment 6. First Embodiment
7. Second Embodiment
8. Third Embodiment
9. Conclusion
10. Configuration example of electronic device
11. Application example to endoscopic surgery system
12. Application example to mobile body
13. Supplement

1. CONFIGURATION EXAMPLE OF THE DISTANCE MEASUREMENT MODULE 1 ACCORDING TO THE EMBODIMENT OF THE PRESENT DISCLOSURE

First, a schematic configuration of the distance measurement module 1 according to the embodiment of the present disclosure will be described with reference to FIG. 1. FIG. 1 is a block diagram illustrating a configuration example of the distance measurement module 1 according to the embodiment of the present disclosure. In detail, as illustrated in FIG. 1, the distance measurement module 1 can mainly include an irradiation unit 20, a light receiving unit 30, a control unit (irradiation control unit) 40, and a processing unit 60. Hereinafter, each functional block included in the distance measurement module 1 according to the present embodiment will be described.

(Irradiation Unit 20)

The irradiation unit 20 includes a light emitting diode (LED) light source (illustration omitted) and an optical element (illustration omitted). The wavelength of emitted light can be changed by appropriately selecting the LED light source. Note that, in the present embodiment, the description will be given assuming that the irradiation unit 20 emits infrared light having a wavelength, for example, in a range of 780 nm to 1000 nm, but the present embodiment is not limited to emitting such infrared light. Further, the irradiation unit 20 can irradiate an object 800 with irradiation light the brightness of which periodically varies in synchronization with a periodic signal such as a rectangular signal supplied from the control unit 40 to be described below.

(Light Receiving Unit 30)

The light receiving unit 30 receives the reflected light reflected from the object 800. The light receiving unit 30 includes a condenser lens (illustration omitted) and a plurality of light receiving elements 10 to be described below. The condenser lens has a function of collecting received light to each light receiving element 10. Further, the light receiving element 10 generates a charge (for example, an electron) on the basis of the intensity of the received light, and synchronizes the generated charge with a periodic signal such as a rectangular signal supplied from the control unit 40 to be described below, and drives internal transistors (sorting transistors VG; see FIG. 3) to transfer to the charge accumulation units MEM (see FIG. 3). Furthermore, the charge transferred to the charge accumulation unit MEM is converted into a signal and finally transferred to the processing unit 60. Note that details of the light receiving element 10 will be described below.

(Control Unit 40)

The control unit 40 supplies a periodic signal to the irradiation unit 20 and the light receiving unit 30, and controls the timing of emission of the irradiation light and the timing of drive of the transistor described above. The frequency of the signal can be, for example, 5 to 20 megahertz (MHz), but is not limited to such a frequency in the present embodiment. Further, the control unit 40 controls the transistors (the sorting transistors VG; see FIG. 3) described above to operate at different timings, for example, different operation.

(Processing Unit 60)

The processing unit 60 can acquire the signal from the light receiving unit 30 and acquire the distance to the object 800 by, for example, an indirect ToF (iToF) method on the basis of the acquired signal. Note that the distance calculation method will be described below.

2. CONFIGURATION EXAMPLE OF THE LIGHT RECEIVING UNIT 30 ACCORDING TO THE EMBODIMENT OF THE PRESENT DISCLOSURE

Figure 2A:
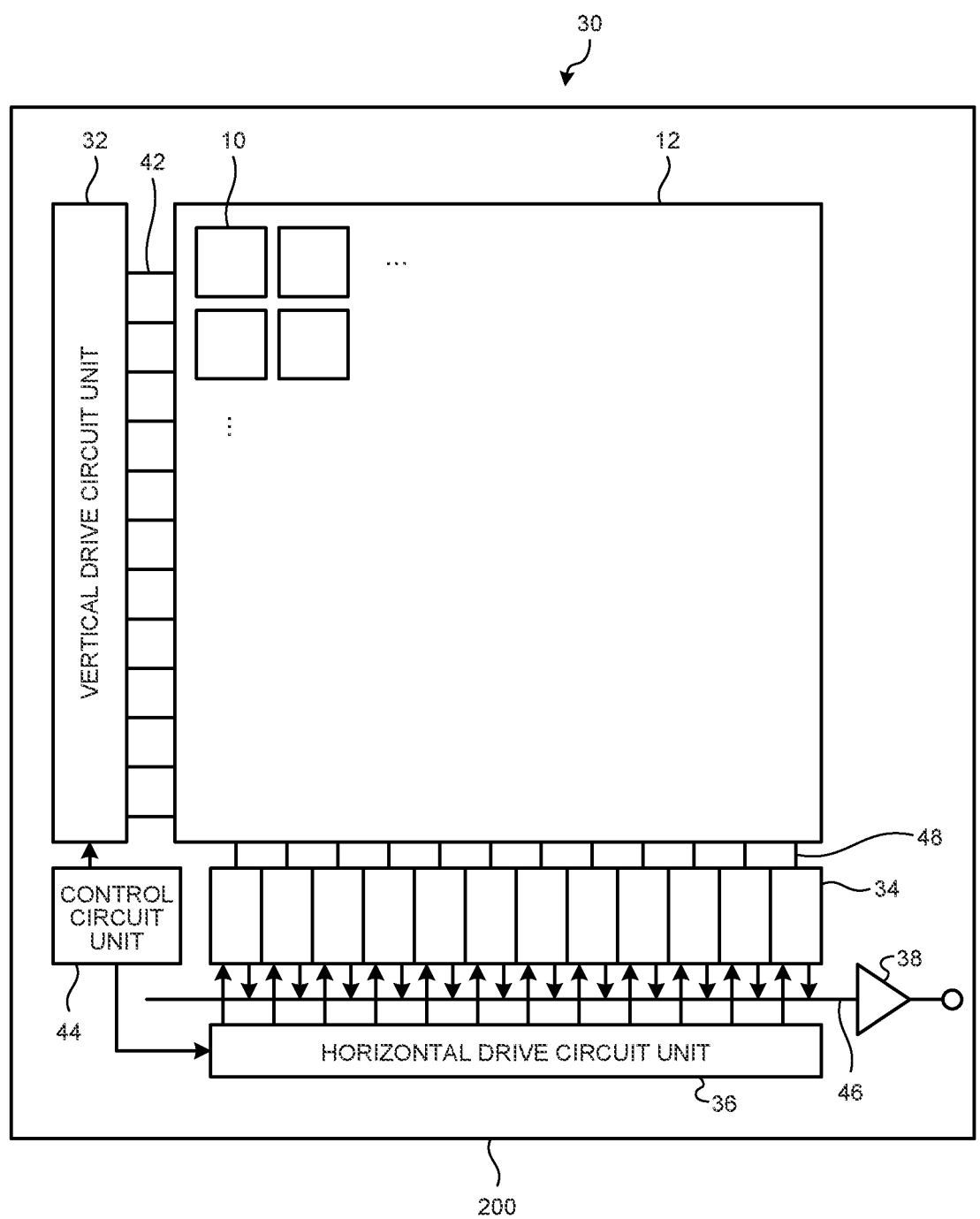
FIG. 2A is an explanatory diagram (No. 1) illustrating a planar configuration example of a light receiving unit 30 according to the embodiment of the present disclosure.
Figure 2B:
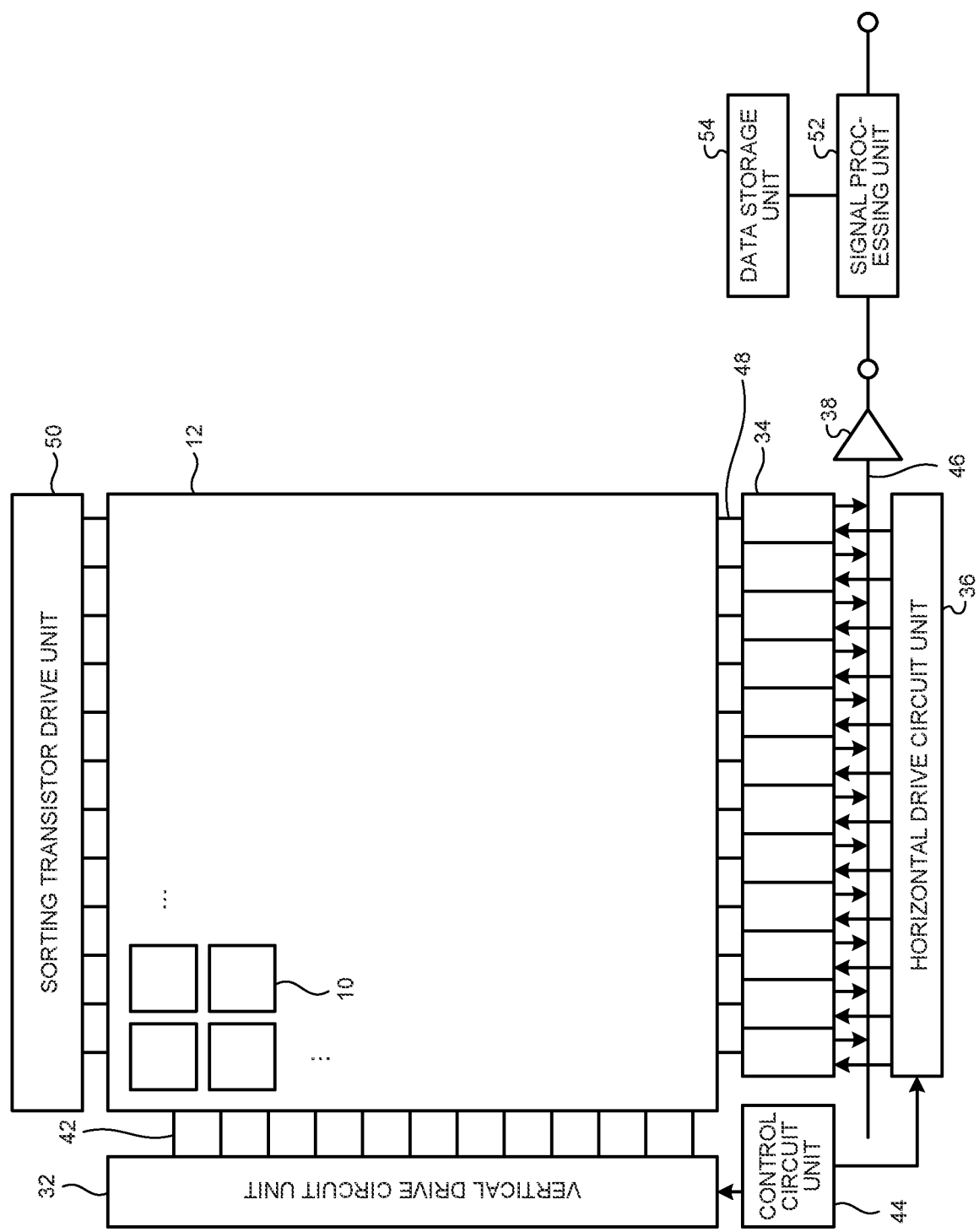
FIG. 2B is an explanatory diagram (No. 2) illustrating a planar configuration example of the light receiving unit 30 according to the embodiment of the present disclosure.
Figure 2C:
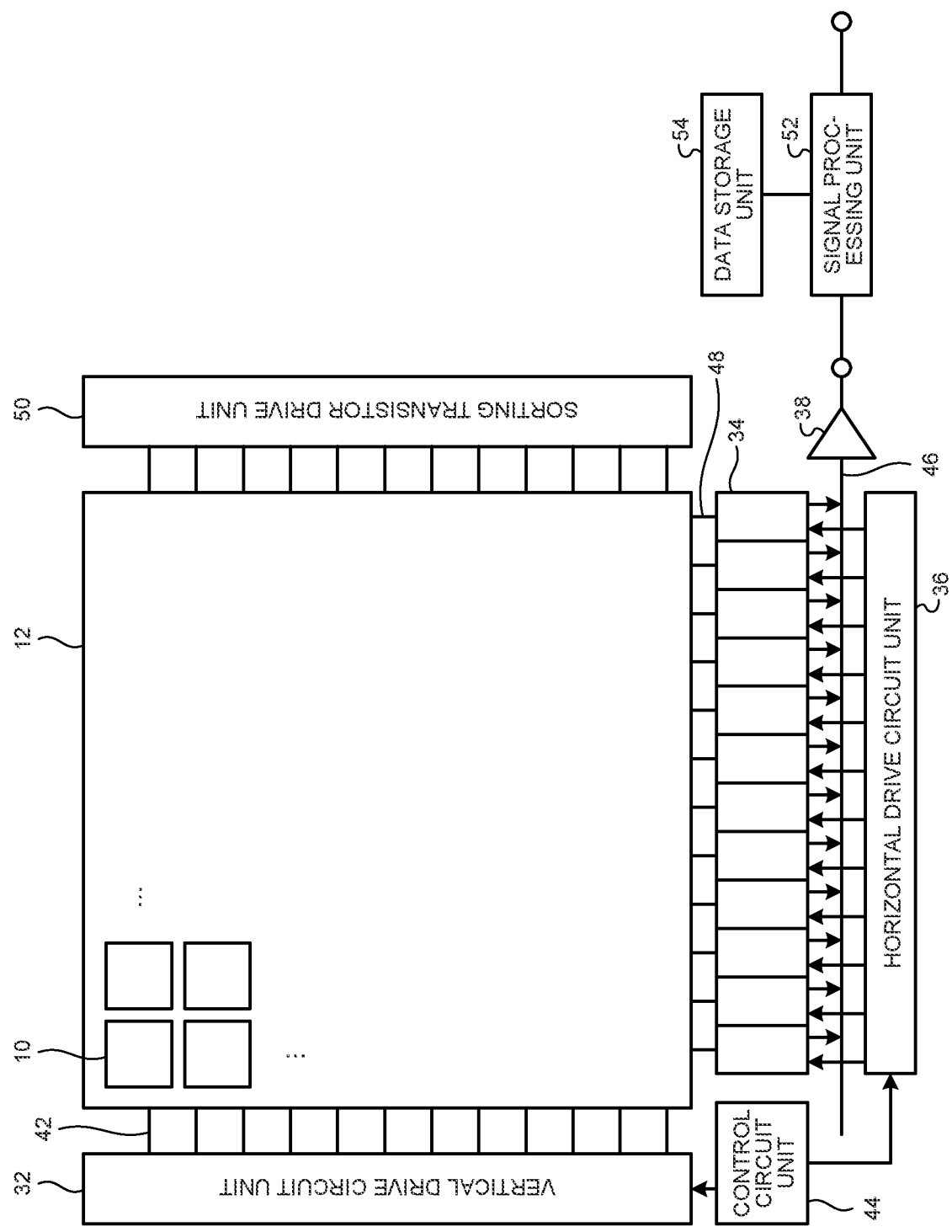
FIG. 2C is an explanatory diagram (No. 3) illustrating a planar configuration example of the light receiving unit 30 according to the embodiment of the present disclosure.

Next, a planar configuration example of the light receiving unit 30 according to the embodiment of the present disclosure will be described with reference to FIGS. 2A to 2C. FIGS. 2A to 2C are explanatory diagrams illustrating a planar configuration example of the light receiving unit 30 according to the embodiment of the present disclosure. In detail, as illustrated in FIG. 2A, the light receiving unit 30 according to the present embodiment includes a pixel array unit 12, a vertical drive circuit unit 32, a column signal processing circuit unit 34, a horizontal drive circuit unit 36, an output circuit unit 38, a control circuit unit 44, and the like provided on a semiconductor substrate 200 made, for example, of silicon. Hereinafter, details of each block of the light receiving unit 30 according to the present embodiment will be described.

(Pixel Array Unit 12)

The pixel array unit 12 includes a plurality of light receiving elements 10 two-dimensionally arranged in a matrix form (a row-column form in the row direction and the column direction) on the semiconductor substrate 200. Each light receiving element 10 includes a photoelectric conversion unit (photodiode PD) (illustration omitted) that converts light into charges (for example, electrons), a plurality of pixel transistors (for example, metal-oxide-semiconductor (MOS) transistors) (illustration omitted), and the like. In other words, the pixel array unit 12 includes a plurality of pixels that photoelectrically converts incident light and outputs a signal according to the resultant charge. Then, the pixel transistors described above can include, for example, transistors having various functions such as a transfer transistor, a selection transistor, a reset transistor, and an amplification transistor. Note that details of the equivalent circuit and the like of the light receiving element 10 will be described below.

Here, the row direction refers to the array direction of the light receiving elements 10 in the horizontal direction, and the column direction refers to the array direction of the light receiving elements 10 in the vertical direction. The row direction is the left-right direction in FIG. 2A, and the column direction is the up-down direction in FIG. 2A. In the pixel array unit 12, a pixel drive wiring 42 is wired along the row direction for each row and a vertical signal line 48 is wired along the column direction for each column with respect to the array of the light receiving elements 10 in the row-column form. For example, the pixel drive wiring 42 transmits a drive signal for performing driving when reading a signal from the light receiving element 10.

(Vertical Drive Circuit Unit 32)

The vertical drive circuit unit 32 includes, for example, a shift register, an address decoder, or the like, selects the pixel drive wiring 42, supplies a pulse for driving the light receiving element 10 to the selected pixel drive wiring 42, and drives all the light receiving elements 10 at the same time or the light receiving element 10 in units of rows. For example, the vertical drive circuit unit 32 selectively scans each light receiving element 10 of the pixel array unit 12 in units of rows sequentially in the vertical direction (up-down direction in FIG. 2A), and supplies a pixel signal based on a charge generated according to the amount of light received by the photodiode PD of each light receiving element 10 to the column signal processing circuit unit 34, which will be described below, through the vertical signal line 48.

(Column Signal Processing Circuit Unit 34)

The column signal processing circuit unit 34 is arranged for each column of the light receiving elements 10, and performs signal processing such as noise removal for each column with respect to the signals output from the light receiving elements 10 of one row. For example, the column signal processing circuit unit 34 performs signal processing such as correlated double sampling (CDS) and analog-digital (AD) conversion in order to remove fixed pattern noise unique to the light receiving element 10.

(Horizontal Drive Circuit Unit 36)

The horizontal drive circuit unit 36 includes, for example, a shift register, an address decoder, or the like, and can sequentially select each of the above-described column signal processing circuit units 34 by sequentially outputting horizontal scanning pulses, and can cause each of the column signal processing circuit units 34 to output a signal to a horizontal signal line 46.

(Output Circuit Unit 38)

The output circuit unit 38 can perform signal processing on the signals sequentially supplied from each of the above-described column signal processing circuit units 34 through the horizontal signal line 46 and output the processed signals. The output circuit unit 38 may function as, for example, a functional unit that performs buffering, or may perform processing such as column variation correction and various digital signal processing. Note that the buffering refers to temporarily storing a signal in order to compensate for a difference in processing speed or transfer speed when a signal is exchanged.

(Control Circuit Unit 44)

The control circuit unit 44 can receive an input clock and data instructing an operation mode and the like, and can output data such as internal information of the light receiving element 10. That is, the control circuit unit 44 generates a clock signal or a control signal serving as a reference of operations of the vertical drive circuit unit 32, the column signal processing circuit units 34, the horizontal drive circuit unit 36, and the like on the basis of a vertical synchronization signal, a horizontal synchronization signal, and a master clock. Then, the control circuit unit 44 outputs the generated clock signal and control signal to the vertical drive circuit unit 32, the column signal processing circuit units 34, the horizontal drive circuit unit 36, and the like.

(Sorting Transistor Drive Unit 50, Signal Processing Unit 52, and Data Storage Unit 54)

As illustrated in FIGS. 2B and 2C, the light receiving element 10 may be provided with a sorting transistor drive unit 50, a signal processing unit 52, and a data storage unit 54. That is, the sorting transistor drive unit 50, the signal processing unit 52, and the data storage unit 54 may be provided on the semiconductor substrate 200. However, the present embodiment is not limited thereto, and the sorting transistor drive unit 50, the signal processing unit 52, and the data storage unit 54 may be provided on another semiconductor substrate (illustration omitted). First, the sorting transistor drive unit 50 controls the operation of sorting transistors VG (see FIG. 3) to be described below. For example, the sorting transistor drive unit 50 may be provided so as to be adjacent to the pixel array unit 12 along the column direction as illustrated in FIG. 2B, or may be provided so as to be adjacent to the pixel array unit 12 along the row direction as illustrated in FIG. 2C, and is not particularly limited in the present embodiment. Further, the signal processing unit 52 has at least an arithmetic processing function, and performs various signal processing such as arithmetic processing on the basis of the signal output from the output circuit unit 38. For signal processing of the signal processing unit 52, the data storage unit 54 temporarily stores data necessary for the processing.

Note that the planar configuration example of the light receiving unit 30 according to the present embodiment is not limited to the examples illustrated in FIGS. 2A to 2C, and may include, for example, other circuits and the like, and is not particularly limited.

3. EQUIVALENT CIRCUIT OF THE LIGHT RECEIVING ELEMENT 10 ACCORDING TO THE EMBODIMENT OF THE PRESENT DISCLOSURE

Figure 3:
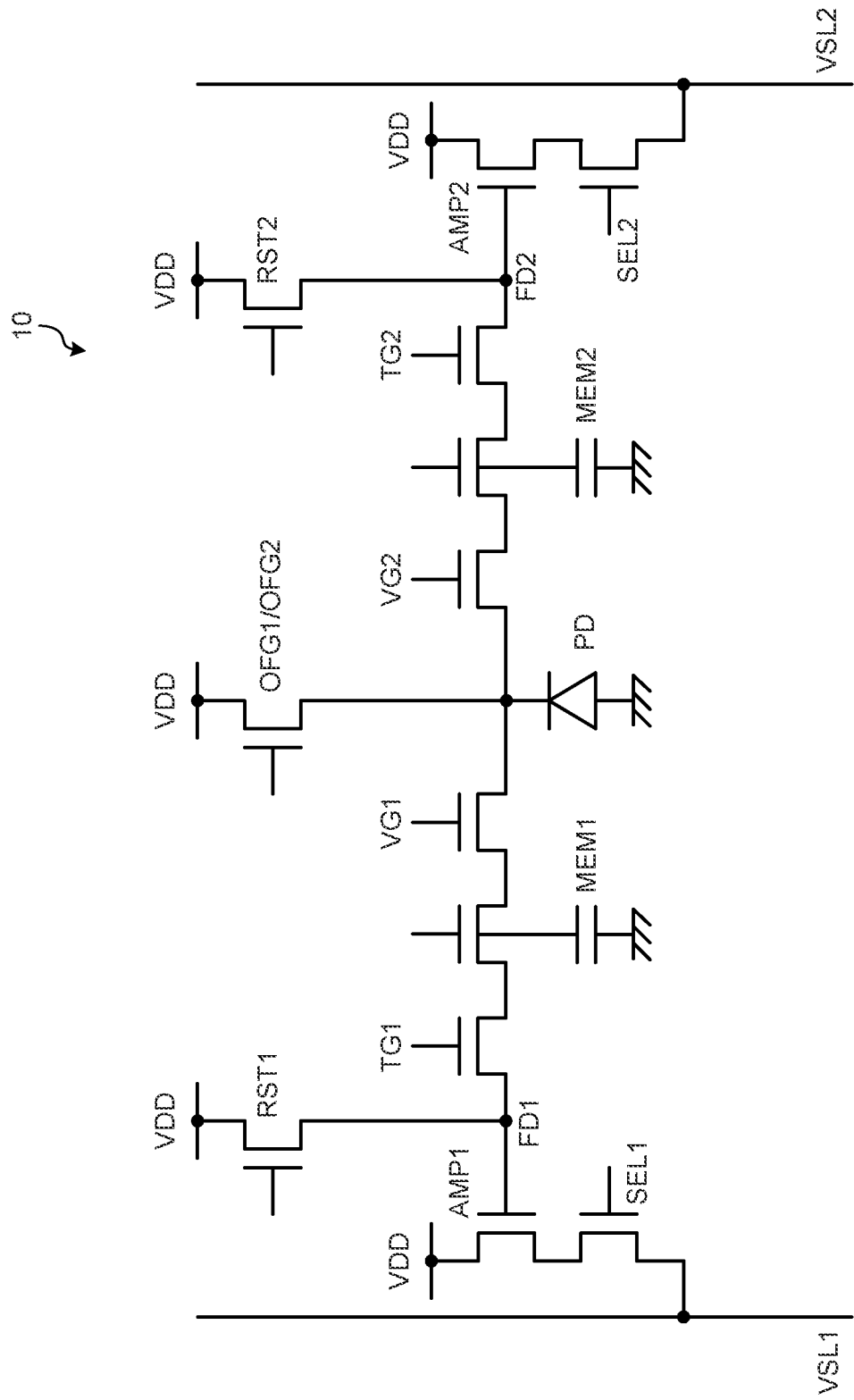
FIG. 3 is an equivalent circuit diagram of a light receiving element 10 according to the embodiment of the present disclosure.

Next, the equivalent circuit of the light receiving element 10 according to the embodiment of the present disclosure will be described with reference to FIG. 3. FIG. 3 is an equivalent circuit diagram of the light receiving element 10 according to the embodiment of the present disclosure.

In detail, as illustrated in FIG. 3, the light receiving element 10 includes the photodiode PD, which is a photoelectric conversion element (photoelectric conversion unit) that changes light into a charge, and a charge discharge transistor OFG (note that, although the charge discharge transistor OFG is illustrated as one transistor on the equivalent circuit, it may include a plurality of transistors electrically connected in parallel). Furthermore, the light receiving element 10 includes two sorting transistors VG, two charge accumulation units (first charge accumulation unit and second charge accumulation unit) MEM, two transfer transistors TG, two floating diffusion regions FD, two reset transistors RST, two amplification transistors AMP, and two selection transistors SEL.

As illustrated in FIG. 3, in the light receiving element 10, one of the source/drain of the charge discharge transistor OFG is electrically connected to the photodiode PD that generates a charge by receiving light. Furthermore, the other of the source/drain of the charge discharge transistor OFG is electrically connected to a power supply circuit (power supply potential VDD). Then, the charge discharge transistor OFG is brought into a conductive state according to a voltage applied to its own gate, and can discharge the charge accumulated in the photodiode PD to the power supply circuit (power supply potential VDD) described above.

Further, as illustrated in FIG. 3, in the light receiving element 10, ones of the sources/drains of the sorting transistors VG1 and VG2 are electrically connected to the photodiode PD, and the others of the sources/drains of the sorting transistors VG1 and VG2 are electrically connected to the charge accumulation units (first charge accumulation unit and second charge accumulation unit) MEM1 and MEM2, respectively. Then, the sorting transistors VG1 and VG2 are brought into a conductive state according to a voltage applied to their own gates (first sorting gate and second sorting gate), and can transfer the charge accumulated in the photodiode PD to the charge accumulation units MEM1 and MEM2, respectively. That is, in the present embodiment, by changing the voltage applied to the gates of the sorting transistors VG1 and VG2 at different timings, the charge accumulated in the photodiode PD can be sorted to one of the two charge accumulation units MEM1 and MEM2. In other words, it can be said that the two charge accumulation units MEM1 and MEM2 share one photodiode PD.

Further, as illustrated in FIG. 3, in the light receiving element 10, ones of sources/drains of the transfer transistors TG1 and TG2 are electrically connected to the others of the sources/drains of the sorting transistors VG1 and VG2 and the charge accumulation units MEM1 and MEM2. Furthermore, the others of the sources/drains of the transfer transistors TG1 and TG2 are electrically connected to the floating diffusion regions FD1 and FD2. Then, the transfer transistors TG1 and TG2 are brought into a conductive state according to a voltage applied to their own gates, and can transfer the charge accumulated in the charge accumulation units MEM1 and MEM2 to the floating diffusion regions FD1 and FD2. Note that, in the embodiment of the present disclosure, since there are two charge accumulation units MEM1 and MEM2, the transfer transistors TG1 and TG2 can share one floating diffusion region FD.

Further, the floating diffusion regions FD1 and FD2 are electrically connected to gates of the amplification transistors AMP1 and AMP2 that convert a charge into a voltage and output it as a signal. Further, ones of sources/drains of the amplification transistors AMP1 and AMP2 are electrically connected to ones of sources/drains of the selection transistors SEL1 and SEL2 that output the aforementioned signal obtained by conversion to signal lines VSL1 and VSL2 according to a selection signal. Furthermore, the others of the sources/drains of the amplification transistors AMP1 and AMP2 are electrically connected to power supply circuits (power supply potentials VDD).

Further, the others of the sources/drains of the selection transistors SEL1 and SEL2 are electrically connected to the aforementioned signal lines VSL1 and VSL2 that transmit the converted voltage as a signal, and are further electrically connected to the above-described column signal processing circuit unit 34. Furthermore, the gates of the selection transistors SEL1 and SEL2 are electrically connected to a selection line (illustration omitted) that selects a row to output a signal, and are further electrically connected to the above-described vertical drive circuit unit 32. That is, the charges accumulated in the floating diffusion regions FD1 and FD2 are converted into voltages by the amplification transistors AMP1 and AMP2 and output to the signal lines VSL1 and VSL2 under the control of the selection transistors SEL1 and SEL2.

Further, as illustrated in FIG. 3, the floating diffusion regions FD1 and FD2 are electrically connected to ones of drains/sources of the reset transistors RST1 and RST2 for resetting the accumulated charges. Gates of the reset transistors RST1 and RST2 are electrically connected to a reset signal line (illustration omitted), and are further electrically connected to the above-described vertical drive circuit unit 32. Further, the others of the drains/sources of the reset transistors RST1 and RST2 are electrically connected to power supply circuits (power supply potentials VDD). Then, the reset transistors RST1 and RST2 are brought into a conductive state according to a voltage applied to their own gates, and can reset the charges accumulated in the floating diffusion regions FD1 and FD2 (discharge to power supply circuits (power supply potentials VDD)).

Note that the equivalent circuit of the light receiving element 10 according to the present embodiment is not limited to the example illustrated in FIG. 3, and may include, for example, other elements and the like, and is not particularly limited.

4. PRINCIPLE OF DISTANCE CALCULATION METHOD USING THE DISTANCE MEASUREMENT MODULE 1 ACCORDING TO THE EMBODIMENT OF THE PRESENT DISCLOSURE

Figure 4:
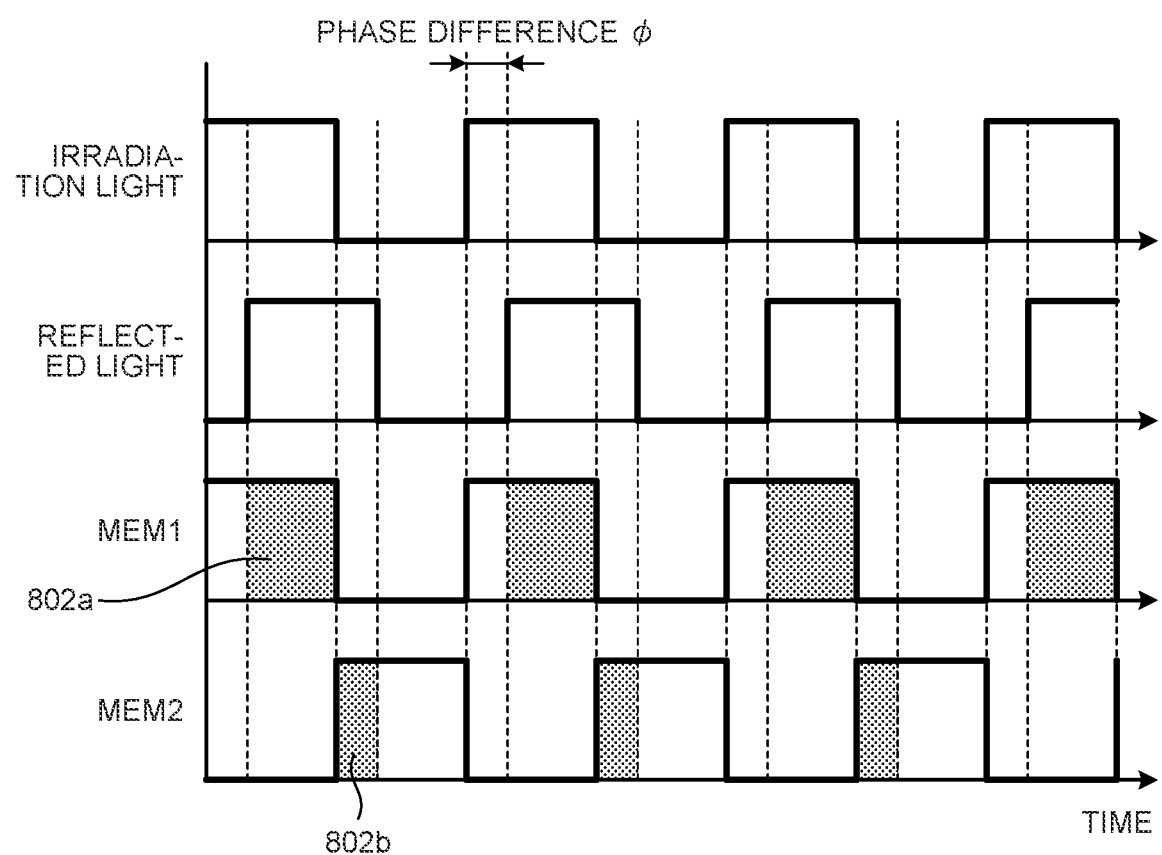
FIG. 4 is an explanatory diagram for explaining the principle of a distance calculation method using the distance measurement module 1 according to the embodiment of the present disclosure.

Next, the principle of a distance calculation method (indirect method) using the distance measurement module 1 according to the embodiment of the present disclosure will be described with reference to FIG. 4. FIG. 4 is an explanatory diagram for explaining the principle of the distance calculation method using the distance measurement module 1 according to the embodiment of the present disclosure, and in detail schematically illustrates a temporal variation in intensity of irradiation light and reflected light in the distance measurement module 1.

As illustrated in FIG. 4, the distance measurement module 1 irradiates the object 800 with light modulated so that the intensity of light periodically varies from the irradiation unit 20. The emitted light is reflected by the object 800 and detected as reflected light by the light receiving unit 30 of the distance measurement module 1. As illustrated in FIG. 4, the detected reflected light (the second stage from the top in FIG. 4) has a phase difference $\phi$ with respect to the irradiation light (the first stage from the top in FIG. 4), and the phase difference $\phi$ increases as the distance from the distance measurement module 1 to the object 800 increases and decreases as the distance from the distance measurement module 1 to the object 800 decreases.

As described above, the light receiving element 10 according to the present embodiment includes, for example, the sorting transistors VG1 and VG2 that operate differently from each other. Therefore, since the periods during which the sorting transistors VG1 and VG2 operate do not overlap, the charges accumulated in the photodiode PD are sorted to the charge accumulation units MEM1 and MEM2 in the periods of regions 802a and 802b indicated by gray in FIG. 4. In detail, the charges sorted to the charge accumulation units MEM1 and MEM2 are transferred to the floating diffusion regions FD1 and FD2, and are finally converted into signals corresponding to areas that are integral values in the periods of the regions 802a and 802b. Thus, as is clear from FIG. 4, the difference between the integral value of the region 802a and the integral value of the region 802b changes according to the phase difference $\phi$ of the reflected light. Thus, in the present embodiment, the distance to the object 800 can be calculated by calculating the phase difference $\phi$ on the basis of the difference between the integral value of the region 802a and the integral value of the region 802b. Note that, in the present embodiment, it is also possible to calculate the distance by calculating the phase difference $\phi$ using not the difference between the integral values but the ratio of the integral values.

5. BACKGROUND LEADING TO CREATION OF THE PRESENT EMBODIMENT

The distance measurement module 1, the light receiving unit 30, the light receiving element 10, and the principle of the distance calculation method according to the embodiment of the present disclosure have been described above. Here, before further describing details of the present embodiment, the background leading to creation of the present embodiment by the present inventors will be described.

As described above, in order to perform distance measurement while ensuring a sufficient S/N ratio, the light receiving element 10 of the light receiving unit 30 of the distance measurement module 1 is required to have a wide dynamic range, that is, to increase an amount of accumulated charges. Furthermore, the light receiving element 10 is required to reduce the influence of kTC noise, which is noise generated by thermal fluctuations of charges in the floating diffusion region FD, that is, to reduce the influence of random noise for highly accurate distance measurement.

Therefore, the present inventors have been led to create the embodiment of the present disclosure in view of the above-described requirements. In detail, in a conventional light receiving element (comparative example described below), the charge generated in a photodiode PD is directly sorted to a floating diffusion region FD. On the other hand, in the embodiment of the present disclosure created by the present inventors, the charge generated in the photodiode PD is not directly sorted to the floating diffusion region FD, but is once sorted to the charge accumulation unit MEM and then transferred to the floating diffusion region FD. In the conventional light receiving element, it is difficult to fully deplete the floating diffusion region FD after the reset operation (an operation of discharging charges (noise) accumulated in a floating charge region FD before accumulating charges generated by light reception). Thus, when the charge (signal) generated in the photodiode PD is transferred to the floating charge region FD, it is difficult to avoid superimposition of kTC noise on the signal. On the other hand, in the present embodiment, as described below, since it is possible to cancel the kTC noise generated in the floating charge region FD, it is possible to reduce the influence of the kTC noise on the charge (signal) generated in the photodiode PD.

Figure 5:
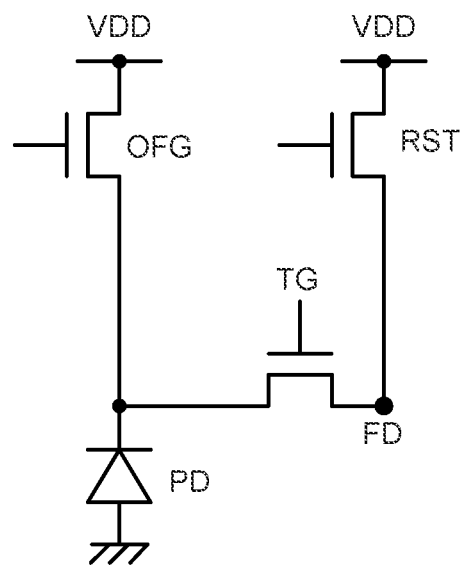
FIG. 5 is an equivalent circuit diagram of a part of a light receiving element according to a comparative example.
Figure 6:
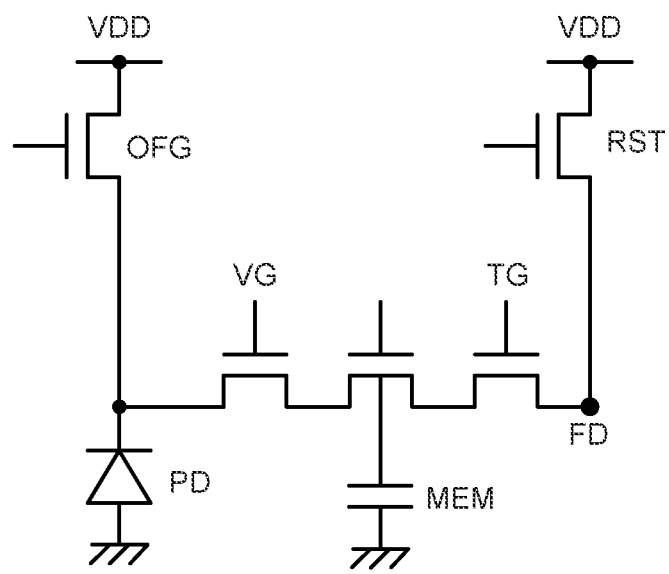
FIG. 6 is an equivalent circuit diagram of a part of the light receiving element 10 according to the embodiment of the present disclosure.

Hereinafter, with reference to FIGS. 5 and 6, the operation of the light receiving element 10 according to the embodiment of the present disclosure will be described in comparison with the operation of the light receiving element according to the comparative example. FIG. 5 is an equivalent circuit diagram of a part of the light receiving element according to the comparative example, and FIG. 6 is an equivalent circuit diagram of a part of the light receiving element 10 according to the embodiment of the present disclosure. Note that, here, the comparative example means a light receiving element that has been repeatedly studied by the present inventors before the embodiment of the present disclosure is made.

First, the kTC noise will be briefly described. As described above, the kTC noise is noise generated by thermal fluctuations of charges. Such kTC noise (charge) is generated in the floating diffusion region FD, but when the floating diffusion region FD can be ideally fully depleted in the reset operation of a global shutter operation (collective reading from all light receiving elements), the kTC noise can be discharged in advance. However, since a high concentration of impurities is implanted into a contact portion of the floating diffusion region FD in order to make an ohmic junction between the floating diffusion region FD and the wiring, it is not possible to perform full depletion even if the reset operation is performed, and it is difficult to fully discharge the kTC noise from the floating diffusion region FD. Thus, when the charge (signal) generated in the photodiode PD is transferred to the floating charge region FD, it is difficult to avoid superimposition of kTC noise on the signal.

An equivalent circuit of the light receiving element according to the comparative example will be described. As illustrated in FIG. 5, the light receiving element according to the comparative example includes a photodiode PD and a charge discharge transistor OFG. Furthermore, the light receiving element includes a transfer transistor TG, a floating diffusion region FD, and a reset transistor RST. More specifically, one of the source/drain of the charge discharge transistor OFG is electrically connected to the photodiode PD, and the other of the source/drain of the charge discharge transistor OFG is electrically connected to a power supply circuit (power supply potential VDD). The charge discharge transistor OFG is brought into a conductive state according to a voltage applied to its own gate, and can discharge the charge accumulated in the photodiode PD. Further, as illustrated in FIG. 5, one of the source/drain of the transfer transistor TG is electrically connected to the photodiode PD, and the other of the source/drain of the transfer transistor TG is electrically connected to the floating diffusion region FD. The transfer transistor TG is brought into a conductive state according to a voltage applied to its own gate, and can transfer the charge generated in the photodiode PD to the floating diffusion region FD. Furthermore, the floating diffusion region FD is electrically connected to one of the drain/source of the reset transistor RST for resetting the accumulated charges. The reset transistor RST is brought into a conductive state according to a voltage applied to its own gate, and can discharge (reset) the charges accumulated in the floating diffusion region FD.

First, in the light receiving element according to the comparative example, the discharge operation of discharging the charge of the photodiode PD is performed before starting light reception. That is, the charge discharge transistor OFG is turned on, and the charge of the photodiode PD is discharged to the power supply circuit (power supply potential VDD). At this time, kTC noise (Nktc) is generated in the floating diffusion region FD.

Next, light reception is started, and a charge (Nsig) (signal) is generated in the photodiode PD. Then, when the transfer transistor TG is turned on, the charge of the photodiode PD is transferred to the floating diffusion region FD. Furthermore, the charge (Nsig, Nktc) accumulated in the floating diffusion region FD is read as a signal.

Next, the discharge operation of discharging the charge in the floating diffusion region FD is performed. That is, the reset transistor RST is turned on, and the charge of the floating diffusion region FD is discharged to the power supply circuit (power supply potential VDD). Furthermore, kTC noise (Nktc) newly generated in the floating diffusion region FD is read.

In the comparative example, the kTC noise (Nktc) newly generated in the floating diffusion region FD is subtracted from the charge (Nsig and Nktc) accumulated in the floating diffusion region FD, so that the charge amount (signal) generated in the photodiode PD by receiving light can be detected. However, since the ktc noise (Nktc) accumulated in the floating diffusion region FD and the kTC noise (Nktc) newly generated in the floating diffusion region FD have different charge amounts, it is difficult to strictly cancel the kTC noise by the subtraction described above. As a result, in the comparative example, a signal from which the kTC noise is fully removed cannot be obtained, and thus it is difficult to ensure high distance measurement accuracy.

Next, an operation of the light receiving element 10 according to the present embodiment will be described. Note that FIG. 6 illustrates an equivalent circuit diagram of a part of the light receiving element 10 according to the embodiment of the present disclosure, but details thereof will not be described here in order to avoid duplication.

First, also in the light receiving element 10 according to the present embodiment, the discharge operation of discharging the charge of the photodiode PD is performed before starting light reception. That is, the charge discharge transistor OFG is turned on, and the charge of the photodiode PD is discharged to the power supply circuit (power supply potential VDD). At this time, kTC noise (Nktc) is generated in the floating diffusion region FD.

Next, light reception is started, and a charge (Nsig) of the photodiode PD is generated. Then, when the sorting transfer transistor VG is turned on, the charge (Nsig) of the photodiode PD is transferred to the accumulation unit MEM.

Next, the discharge operation of discharging the kTC noise (Nktc) in the floating diffusion region FD is performed. That is, the reset transistor RST is turned on, and the kTC noise (Nktc) of the floating diffusion region FD is discharged to the power supply circuit (power supply potential VDD).

Next, the kTC noise (Nktc) generated in the floating diffusion region FD is read.

Then, the transfer transistor TG is turned on, and the charge (Nsig) (signal) accumulated in the accumulation unit MEM is transferred to the floating diffusion region FD. Then, the charge (Nsig, Nktc) accumulated in the floating diffusion region FD is read as a signal.

In the present embodiment, the kTC noise (Nktc) generated in the floating diffusion region FD is subtracted from the charge (Nsig and Nktc) accumulated in the floating diffusion region FD, so that the charge amount (signal) generated in the photodiode PD by receiving light can be detected. That is, in the present embodiment, since the charge amount of the kTC noise included in the signal can be figured out, the kTC noise can be canceled. As a result, in the present embodiment, a signal from which the kTC noise is removed can be obtained, and thus it is possible to ensure high distance measurement accuracy.

Furthermore, in the embodiment of the present disclosure created by the present inventors, the charge accumulation unit MEM described above includes a metal-oxide-semiconductor (MOS) type capacitance. That is, in the present embodiment, the charge accumulation unit MEM includes a MOS-type capacitance including a stack of an electrode made of a metal film or a polysilicon film, an insulating film made of an oxide film, and a semiconductor region. In the present embodiment, it is possible to easily increase the capacitance of the accumulation unit MEM by increasing the area of the interface of the stack described above. Thus, according to the present embodiment, the capacitance value can be further increased, and a wide dynamic range can be ensured. The details of the embodiment of the present disclosure created by the present inventors will be sequentially described below.

6. FIRST EMBODIMENT

6.1 Planar Structure

Figure 7:
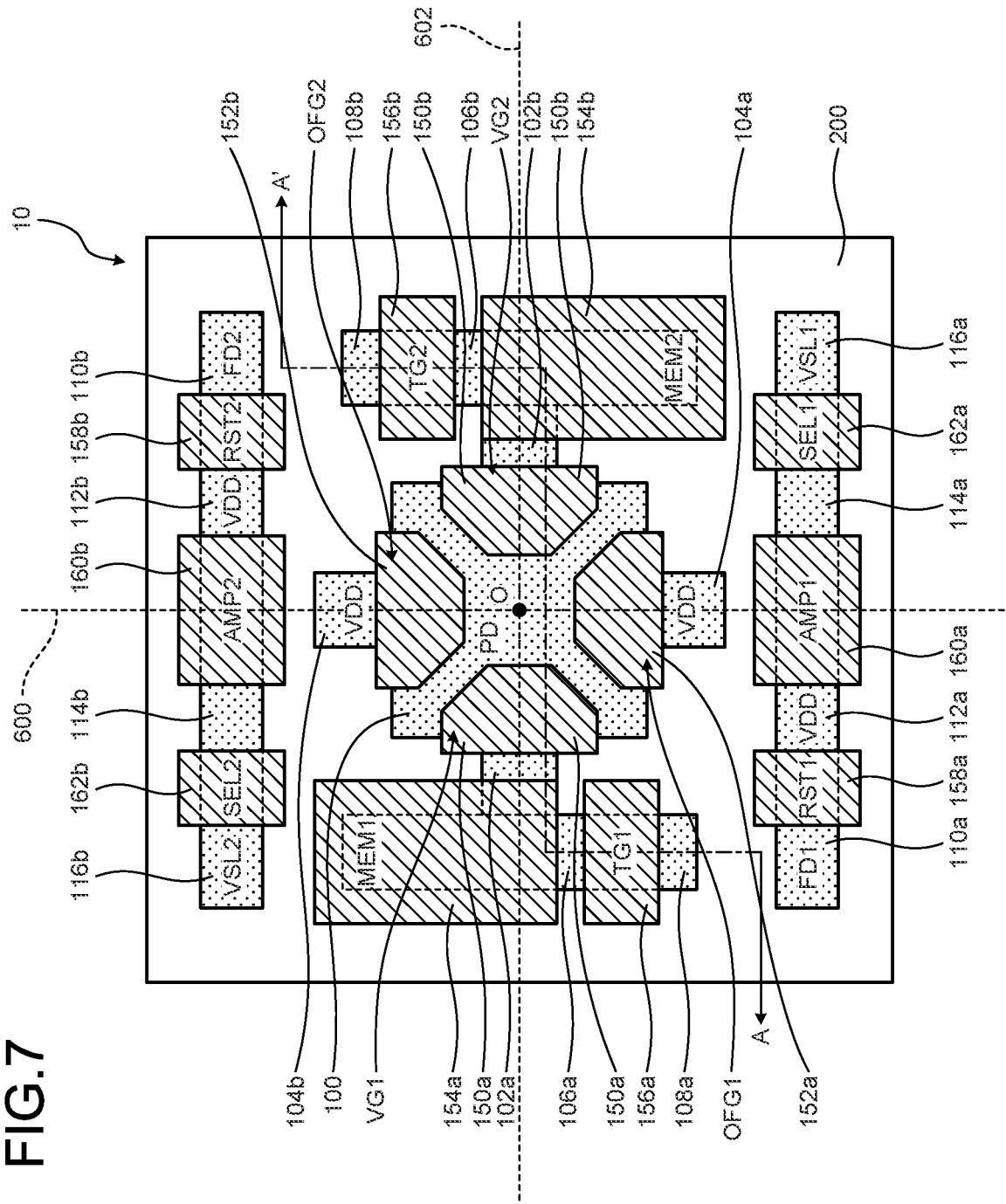
FIG. 7 is an explanatory diagram illustrating a planar configuration example of the light receiving element 10 according to a first embodiment of the present disclosure.

First, a planar structure example of the light receiving element 10 according to the first embodiment of the present disclosure will be described with reference to FIG. 7. FIG. 7 is an explanatory diagram illustrating a planar configuration example of the light receiving element 10 according to the present embodiment, and is a diagram of the light receiving element 10 when viewed from above the front surface of the semiconductor substrate 200. Note that the left-right direction in FIG. 7 corresponds to the row direction (left-right direction) in FIG. 2A, and the up-down direction in FIG. 7 corresponds to the column direction (up-down direction) in FIG. 2A.

As illustrated in FIG. 7, an N-type semiconductor region 100 is formed in a P-type semiconductor substrate 200 in a central portion of the light receiving element 10, and the N-type semiconductor region 100 constitutes a part of the photodiode (photoelectric conversion unit) PD. Furthermore, gate electrodes 150a and 150b of the sorting transistors VG1 and VG2 are arranged so as to be line-symmetric (substantially line-symmetric) relative to a center line 600 passing through a center point (center) O of the photodiode PD and extending along the up-down direction (column direction) over the light receiving element 10. Note that the gate electrodes 150a and 150b of the sorting transistors VG1 and VG2 are provided so as to overlap at least a part of the N-type semiconductor region 100.

In detail, the sorting transistor VG1 includes the gate electrode 150a, a gate insulating film (illustration omitted) located between the gate electrode 150a and the semiconductor substrate 200, the N-type semiconductor region 100, which is a source region, and an N-type semiconductor region 102a, which is a drain region. The N-type semiconductor region 100, which is a source region, is also used as the photodiode PD, and the N-type semiconductor region 102a, which is a drain region, is also used as the charge accumulation unit MEM1. Further, the sorting transistor VG2 is similar to the sorting transistor VG1.

Furthermore, as illustrated in FIG. 7, gate electrodes 152a and 152b of charge discharge transistors OFG1 and OFG2 are arranged so as to be line-symmetric (substantially line-symmetric) relative to a center line 602 passing through the center point O of the photodiode PD and extending along the left-right direction (row direction) over the light receiving element 10. Note that the gate electrodes 152a and 152b of the charge discharge transistors OFG1 and OFG2 are provided so as to overlap at least a part of the N-type semiconductor region 100.

In detail, the charge discharge transistor OFG1 includes the gate electrode 152a, a gate insulating film (illustration omitted) located between the gate electrode 152a and the semiconductor substrate 200, the N-type semiconductor region 100, which is a source region, and an N-type semiconductor region 104a, which is a drain region. The N-type semiconductor region 100, which is a source region, is also used as the photodiode PD. Further, the charge discharge transistor OFG2 is similar to the charge discharge transistor OFG1.

In addition, the charge accumulation units MEM1 and MEM2 and the transfer transistors TG1 and TG2 are provided so as to be mirror-symmetrical with reference to the center line 600 and to sandwich the N-type semiconductor regions 102 and the sorting transistors VG1 and VG2 from both sides. Note that the charge accumulation unit MEM1 is arranged adjacent to the transfer transistor TG1 along the up-down direction (column direction) in FIG. 7, and the charge accumulation unit MEM2 is arranged adjacent to the transfer transistor TG2 along the up-down direction (column direction) in FIG. 7.

In detail, the charge accumulation unit MEM1 includes, for example, an electrode 154a, an insulating film (illustration omitted) provided below the electrode 154a, and the N-type semiconductor region 102a provided below the insulating film, and the detailed structure thereof will be described below. Further, the transfer transistor TG1 includes a gate electrode 156a, a gate insulating film (illustration omitted) located between the gate electrode 156a and the semiconductor substrate 200, an N-type semiconductor region 106a, which is a source region, and an N-type semiconductor region 108a, which is a drain region. Further, the charge accumulation unit MEM2 and the transfer transistor TG2 are similar to the charge accumulation unit MEM1 and the transfer transistor TG1.

Furthermore, the reset transistors RST1 and RST2, the amplification transistors AMP1 and AMP2, and the selection transistors SEL1 and SEL2 are arranged so as to be mirror-symmetrical with reference to the center line 602 and so as to sandwich the N-type semiconductor regions 102 and the charge discharge transistors OFG1 and OFG2 from both sides. Note that the reset transistor RST1, the amplification transistor AMP1, and the selection transistor SEL1 are arranged so as to be adjacent to each other along the left-right direction (row direction) in FIG. 7, and the reset transistor RST2, the amplification transistor AMP2, and the selection transistor SEL2 are also arranged so as to be adjacent to each other along the left-right direction (row direction) in FIG. 7.

In detail, the reset transistor RST1 includes a gate electrode 158a, a gate insulating film (illustration omitted) located between the gate electrode 158a and the semiconductor substrate 200, an N-type semiconductor region 110a, which is a source region, and an N-type semiconductor region 112a, which is a drain region. The N-type semiconductor region 110a, which is a source region, is also used as the floating diffusion region FD1, and the N-type semiconductor region 112a, which is a drain region, is also used as the amplification transistor AMP1. Further, the reset transistor RST2 is similar to the reset transistor RST1.

Further, the amplification transistor AMP1 includes a gate electrode 160a, a gate insulating film (illustration omitted) located between the gate electrode 160a and the semiconductor substrate 200, the N-type semiconductor region 112a, which is a drain region, and an N-type semiconductor region 114a, which is a source region. The N-type semiconductor region 112a, which is a drain region, is also used as the drain region of the reset transistor RST1. Further, the amplification transistor AMP2 is similar to the amplification transistor AMP1.

Furthermore, the selection transistor SEL1 includes a gate electrode 162a, a gate insulating film (illustration omitted) located between the gate electrode 162a and the semiconductor substrate 200, the N-type semiconductor region 114a, which is a drain region, and an N-type semiconductor region 116a, which is a source region. The N-type semiconductor region 114a, which is a drain region, is also used as the source region of the amplification transistor AMP1. Further, the selection transistor SEL2 is similar to the selection transistor SEL1.

Note that the planar structure of the light receiving element 10 according to the present embodiment is not limited to the example illustrated in FIG. 7, and may include, for example, other elements and the like, and is not particularly limited.

6.2 Cross-Sectional Structure

Figure 8:
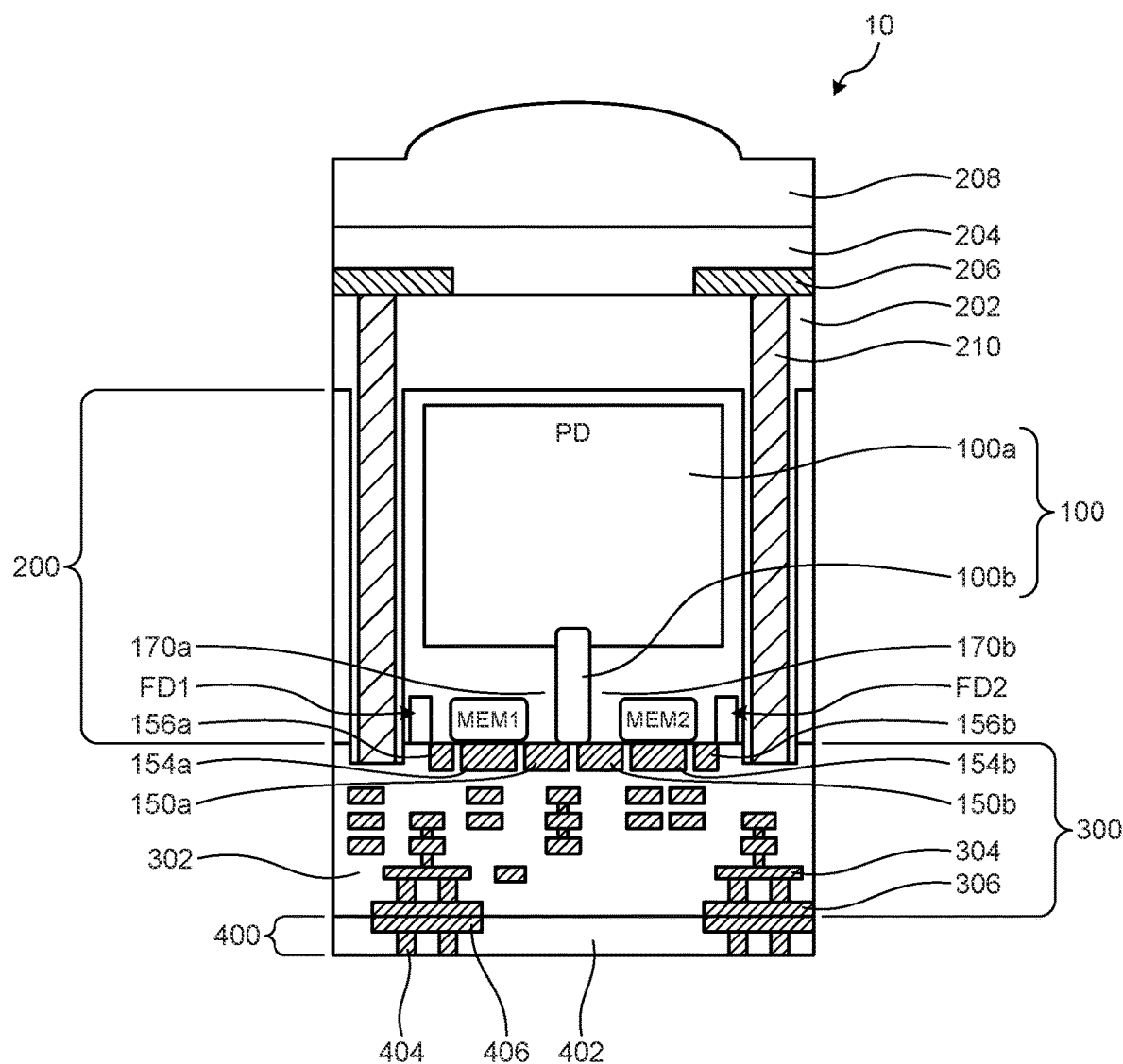
FIG. 8 is a cross-sectional diagram of the light receiving element 10 cut along line A-A' in FIG. 7.

Next, a cross-sectional structure example of the light receiving element 10 according to the first embodiment of the present disclosure will be described with reference to FIG. 8. FIG. 8 is a cross-sectional diagram of the light receiving element 10 cut along line A-A' in FIG. 7, and in detail, the upper side in FIG. 8 is the back surface side of the semiconductor substrate 200, and the lower side in FIG. 8 is the front surface side of the semiconductor substrate 200.

First, as illustrated in FIG. 8, the light receiving element 10 includes the semiconductor substrate 200 made of a silicon substrate or the like. In detail, the photodiode PD is formed in the semiconductor substrate 200 by forming N-type semiconductor regions 100a and 100b in the P-type semiconductor substrate 200.

Next, description will be given from the upper side in FIG. 8, that is, the back surface side of the semiconductor substrate 200. An on-chip lens 208 made of a styrene-based resin, an acrylic resin, a styrene-acrylic copolymer resin, a siloxane-based resin, or the like, on which reflected light from the object 800 is incident, is provided above the back surface of the semiconductor substrate 200. A planarization film 204 made of, for example, silicon oxide ($SiO_2$), silicon nitride (SiN), silicon oxynitride (SiON), or the like is provided below the on-chip lens 208. Furthermore, an antireflection film 202 made of an insulating film is provided below the planarization film 204. For example, the antireflection film 202 can be formed of hafnium oxide ($HfO_2$), aluminum oxide ($Al_2O_3$), titanium oxide ($TiO_2$), silicon oxide, or the like, or a stack thereof.

A light shielding film 206 that prevents reflected light from the object 800 from being incident on an adjacent light receiving element 10 is provided in a boundary region with the adjacent light receiving element 10 above the antireflection film 202. The light shielding film 206 is made of a light shielding material, and can be formed using, for example, a metal material such as tungsten (W), aluminum (Al), or copper (Cu).

Furthermore, below the light shielding film 206, a pixel isolation portion (first pixel isolation portion) 210 (FFTI) that penetrates the semiconductor substrate 200 and prevents incident light from entering the adjacent light receiving element 10 is provided. The pixel isolation portion 210 includes, for example, a trench penetrating from the back surface to the front surface of the semiconductor substrate 200, and an insulating film such as silicon oxide or a metal film such as aluminum embedded in the trench.

Next, description will be given of the lower side in FIG. 8, that is, the front surface side of the semiconductor substrate 200. The two sorting transistors VG1 and VG2, which are vertical transistors, are formed so as to sandwich the N-type semiconductor region 100b. In detail, the sorting transistors VG1 and VG2 respectively include the gate electrodes 150a and 150b made of, for example, a polysilicon film provided on the front surface of the semiconductor substrate 200.

Furthermore, the charge accumulation units MEM1 and MEM2 are provided in the semiconductor substrate 200 so as to sandwich the sorting transistors VG1 and VG2 in the left-right direction. For example, the charge accumulation units MEM1 and MEM2 can be metal-oxide-semiconductor (MOS)-type capacitances including a stack of electrodes 154a and 154b made of a metal film or a polysilicon film, an insulating film (illustration omitted) made of an oxide film, and N-type semiconductor regions 102a and 102b (in FIG. 8, illustrated as MEM1 and MEM2). Details of the charge accumulation units MEM1 and MEM2 will be described below.

Then, gate electrodes 156a and 156b of the transfer transistors TG1 and TG2 are provided on the front surface of the semiconductor substrate 200 adjacent to the charge accumulation units MEM1 and MEM2. Furthermore, N-type semiconductor regions 110a and 110b illustrated as the floating diffusion regions FD1 and FD2 are formed in the semiconductor substrate 200 close to the gate electrodes 156a and 156b of the transfer transistors TG1 and TG2.

Furthermore, a wiring layer 300 is provided on the front surface of the semiconductor substrate 200. The wiring layer 300 includes an insulating film 302 and a metal film 304. Furthermore, an electrode 306 is provided on the surface of the wiring layer 300 opposite to the semiconductor substrate 200.

In addition, a substrate 400 is provided on the surface of the wiring layer 300 opposite to the semiconductor substrate 200. The substrate 400 also includes an insulating film 402 and a metal film 404, and an electrode 406 is provided on the surface on the wiring layer 300 side. For example, when the electrode 306 of the wiring layer 300 and the electrode 406 of the substrate 400 are formed of copper (Cu) or the like and are in contact with each other, the wiring layer 300 and the substrate 400 can be joined.

Note that the cross-sectional structure of the light receiving element 10 according to the present embodiment is not limited to the example illustrated in FIG. 8, and may include, for example, other elements and the like, and is not particularly limited.

Figure 9:
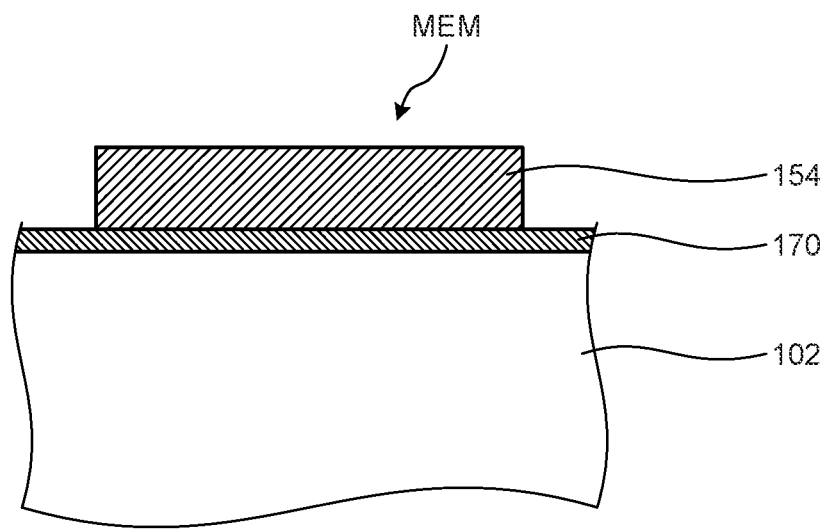
FIG. 9 is an explanatory diagram illustrating a cross-sectional configuration example of a charge accumulation unit MEM according to the first embodiment of the present disclosure.
Figure 10:
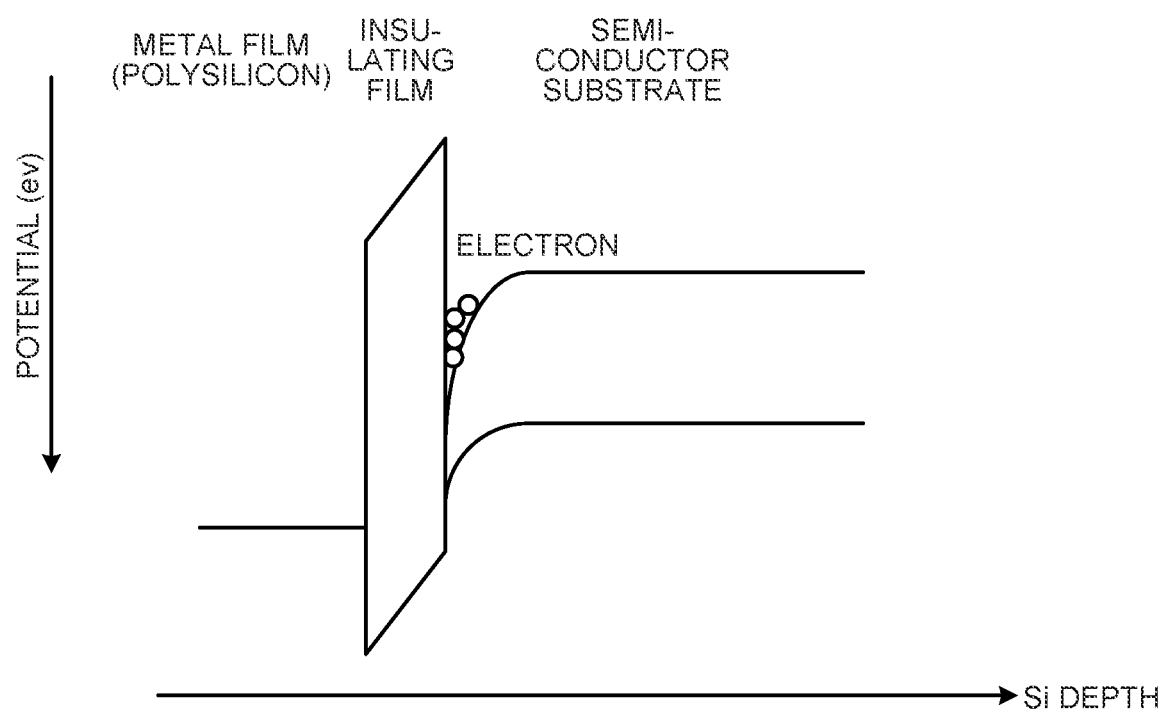
FIG. 10 is an energy band diagram of the charge accumulation unit MEM of FIG. 9.

Next, details of the charge accumulation unit MEM according to the present embodiment will be described with reference to FIGS. 9 and 10. FIG. 9 is an explanatory diagram illustrating a cross-sectional configuration example of the charge accumulation unit MEM according to the present embodiment and corresponds to the cross-sectional diagram of FIG. 8. Further, FIG. 10 is an energy band diagram of the charge accumulation unit MEM of FIG. 9. Note that, in FIG. 9, the upper side in FIG. 9 is the front surface side of the semiconductor substrate 200, and the lower side in FIG. 9 is the back surface side of the semiconductor substrate 200.

As illustrated in FIG. 9, the charge accumulation unit MEM according to the present embodiment includes an insulating layer 170 and an electrode 154 stacked on the semiconductor substrate (semiconductor layer) 200. The electrode 154 is made of various metal films or polysilicon films, and the insulating layer 170 is made of an oxide film such as a silicon oxide film. In the charge accumulation unit MEM, by applying a positive voltage (on-voltage) to the electrode, a depletion layer (inversion region) is generated on the outermost surface of the semiconductor substrate (semiconductor layer) 200 located immediately below the electrode (metal film or polysilicon film) 154 and the insulating layer 170 as illustrated in FIG. 10. Then, the charge is transferred to the generated depletion layer, and the charge is attracted to and accumulated in the electrode 154. In the present embodiment, it is possible to easily increase the capacitance of the charge accumulation unit MEM by increasing the area of the electrode 154 (area in contact with the semiconductor substrate).

Furthermore, in the present embodiment, the capacitance of the charge accumulation unit MEM can be further increased by reducing the film thickness of the insulating layer 170 or forming the insulating layer 170 using a material having a high relative dielectric constant (hafnium oxide ($HfO_2$)).

Figure 11:
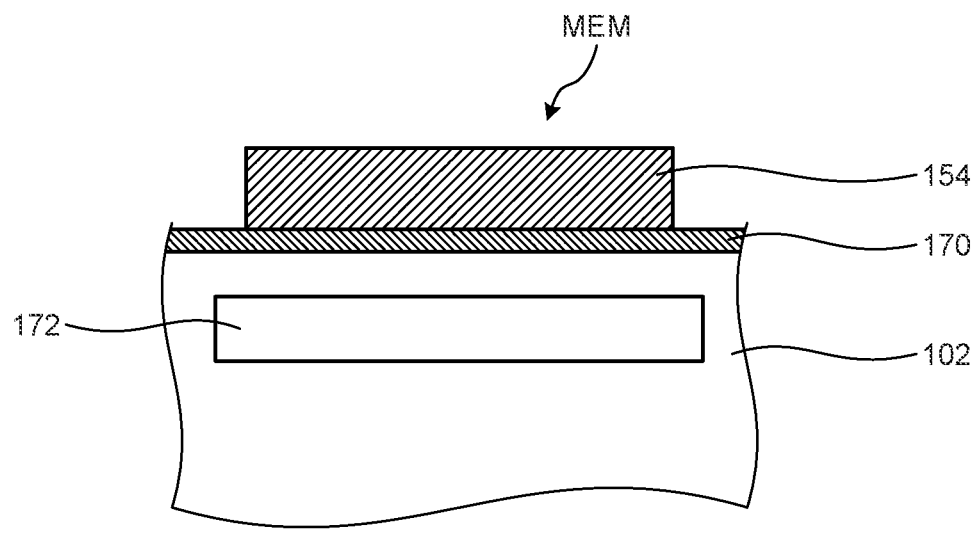
FIG. 11 is an explanatory diagram illustrating another cross-sectional configuration example of the charge accumulation unit MEM according to the first embodiment of the present disclosure.
Figure 12:
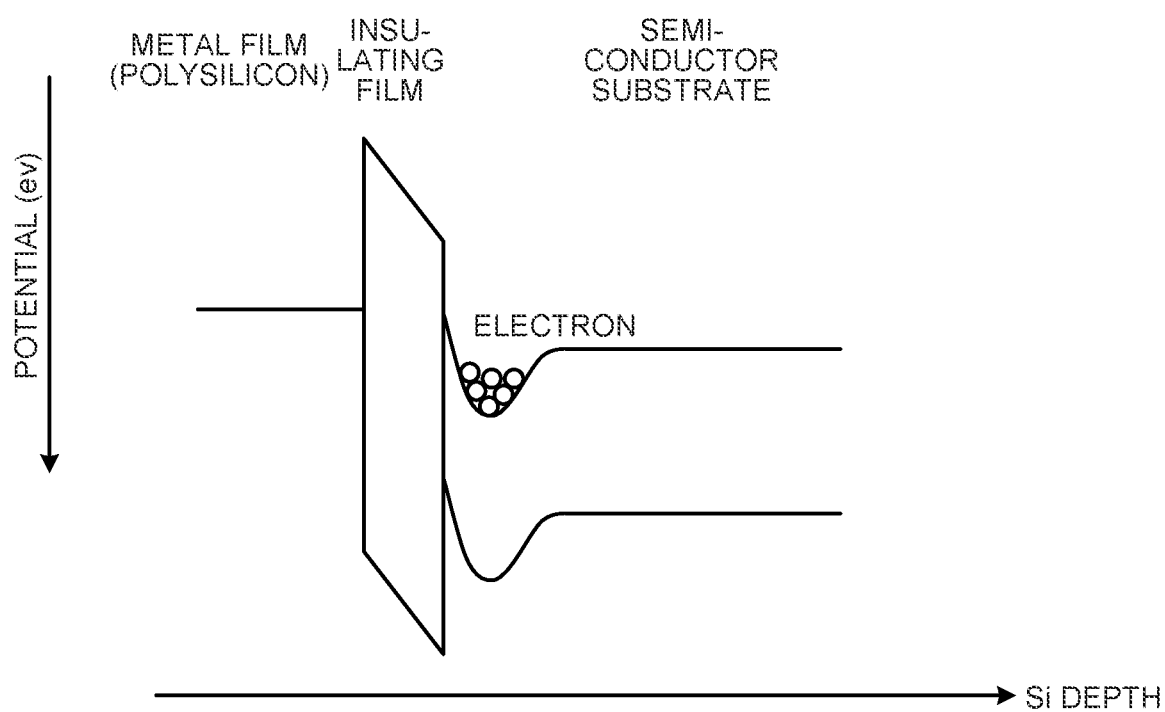
FIG. 12 is an energy band diagram of the charge accumulation unit MEM of FIG. 11.

Further, in the charge accumulation unit MEM as illustrated in FIG. 9, since the charge moves on the outermost surface of the semiconductor substrate 200, there is a possibility that the charge is captured by a defect (for example, a dangling bond) generated on the surface and disappears or transfer of the charge to the floating diffusion region FD is delayed. Therefore, in the present embodiment, a structure of the charge accumulation unit MEM capable of accumulating charges in a deep region of the semiconductor substrate 200 may be adopted in order to avoid such charge capture and the like. Details of such charge accumulation unit MEM will be described below with reference to FIGS. 11 and 12. FIG. 11 is an explanatory diagram illustrating another cross-sectional configuration example of the charge accumulation unit MEM according to the present embodiment, and FIG. 12 is an energy band diagram of the charge accumulation unit MEM of FIG. 11. Note that, in FIG. 11, the upper side in FIG. 11 is the front surface side of the semiconductor substrate 200, and the lower side in FIG. 9 is the back surface side of the semiconductor substrate 200.

As illustrated in FIG. 11, the charge accumulation unit MEM according to the present embodiment includes the insulating layer 170 and the electrode 154 stacked on the semiconductor substrate (semiconductor layer) 200. Furthermore, the charge accumulation unit MEM includes an embedded layer 172 embedded in the semiconductor substrate 200 between the insulating layer 170 and the semiconductor substrate 200. For example, in a case where the semiconductor substrate 200 is a P-type semiconductor substrate, the embedded layer 172 is an N-type semiconductor region into which an N-type impurity is introduced.

In the charge accumulation unit MEM, by applying, for example, a negative voltage (off-voltage) to the electrode, a depletion layer (channel region) is generated in the embedded layer 172 embedded in the semiconductor substrate 200 as illustrated in FIG. 12. Then, charges are accumulated in the generated depletion layer. Note that the depth at which the depletion layer is generated can be adjusted by appropriately selecting the impurity concentrations of the semiconductor substrate 200 and the embedded layer 172, the thickness of the embedded layer 172, the thickness of the insulating layer 170, and the like. In this way, in the present embodiment, it is possible to avoid the charge from being captured by the defect or the like on the outermost surface, and the mobility of the charge can be increased.

As described above, according to the present embodiment, it is possible to provide the light receiving element 10 capable of reducing the influence of kTC noise while ensuring a wide dynamic range.

6.3 Variation Examples

Note that the light receiving element 10 according to the embodiment of the above-described present disclosure can be modified as described below. A first variation example to a fifth variation example of the present embodiment will be described below. Each of light receiving elements 10 according to the first variation example to the fifth variation example described below includes charge accumulation units MEM1 and MEM2 each including a MOS capacitance.

First Variation Example

Figure 13:
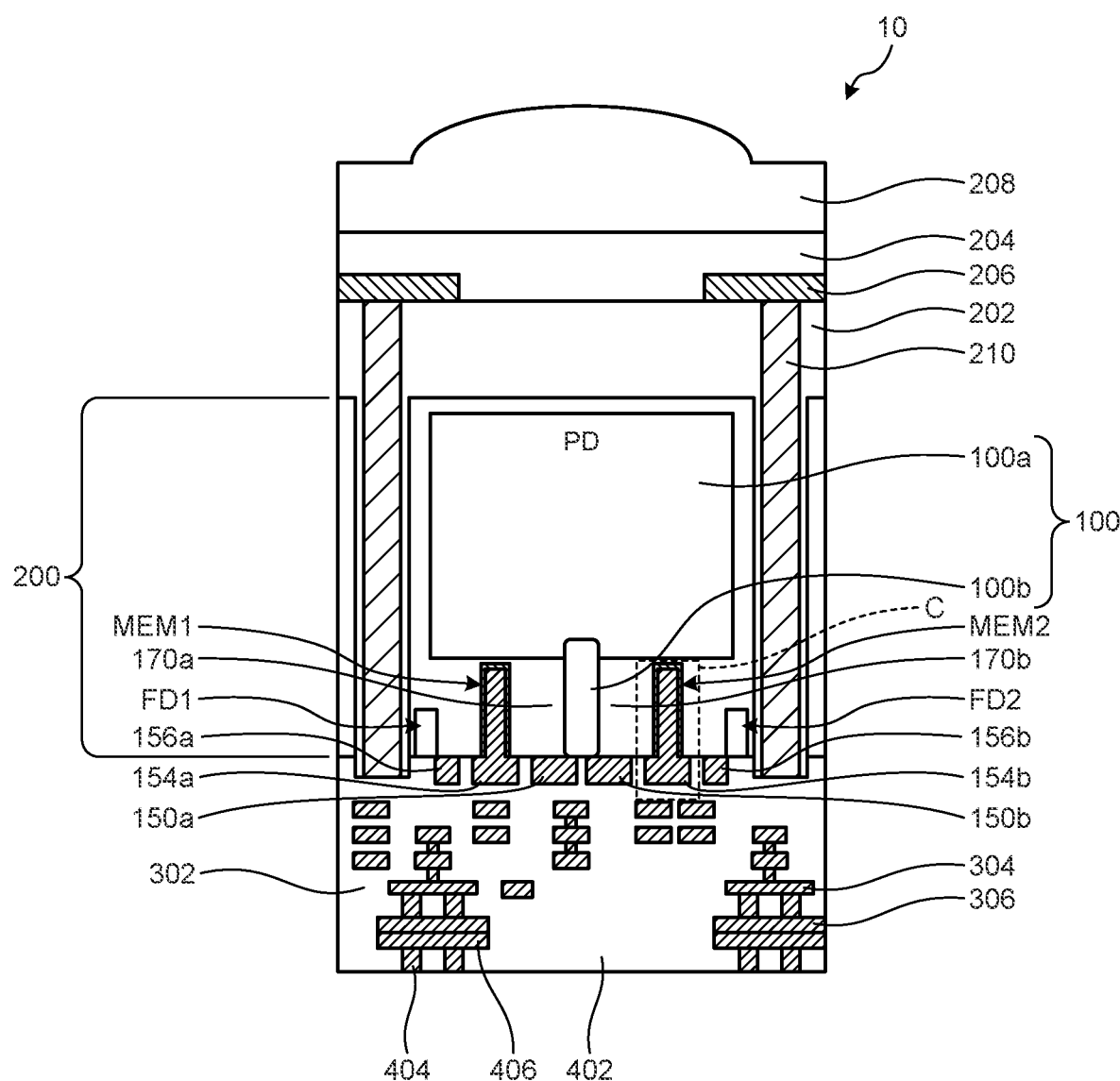
FIG. 13 is an explanatory diagram illustrating a cross-sectional configuration example of a light receiving element 10 according to a first variation example of the same embodiment.
Figure 14:
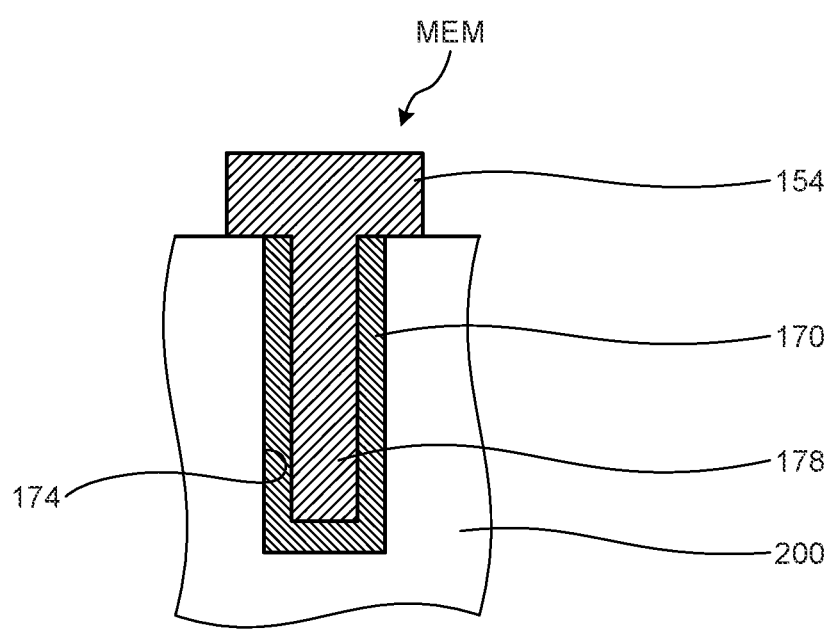
FIG. 14 is an enlarged diagram of a region C in FIG. 13.

First, the first variation example will be described with reference to FIGS. 13 and 14. FIG. 13 is an explanatory diagram illustrating a cross-sectional configuration example of the light receiving element 10 according to the first variation example of the present embodiment, and FIG. 14 is an enlarged diagram of a region C in FIG. 13. In the present variation example, the charge accumulation units MEM1 and MEM2 including a MOS capacitance are provided, but unlike the above-described present embodiment, as illustrated in FIG. 13, a vertical electrode 154 embedded in a semiconductor substrate 200 is provided. In detail, as illustrated in FIG. 14, an insulating layer 170 embedded in a trench 174 formed in the semiconductor substrate 200 and a vertical embedded electrode portion 178 embedded in the insulating layer 170 are provided. According to the present variation example, since the charge accumulation units MEM1 and MEM2 have the vertical electrode 154, the area of the insulating layer 170 sandwiched between the vertical electrode 154 and the semiconductor substrate (in detail, the N-type semiconductor regions 102a and 102b) 200 facing the electrode 154 can be increased. As a result, according to the present variation example, since the area is increased, the capacitance of the charge accumulation units MEM1 and MEM2 can be further increased, and eventually, a wide dynamic range of the light receiving element 10 can be ensured.

Second Variation Example

Figure 15:
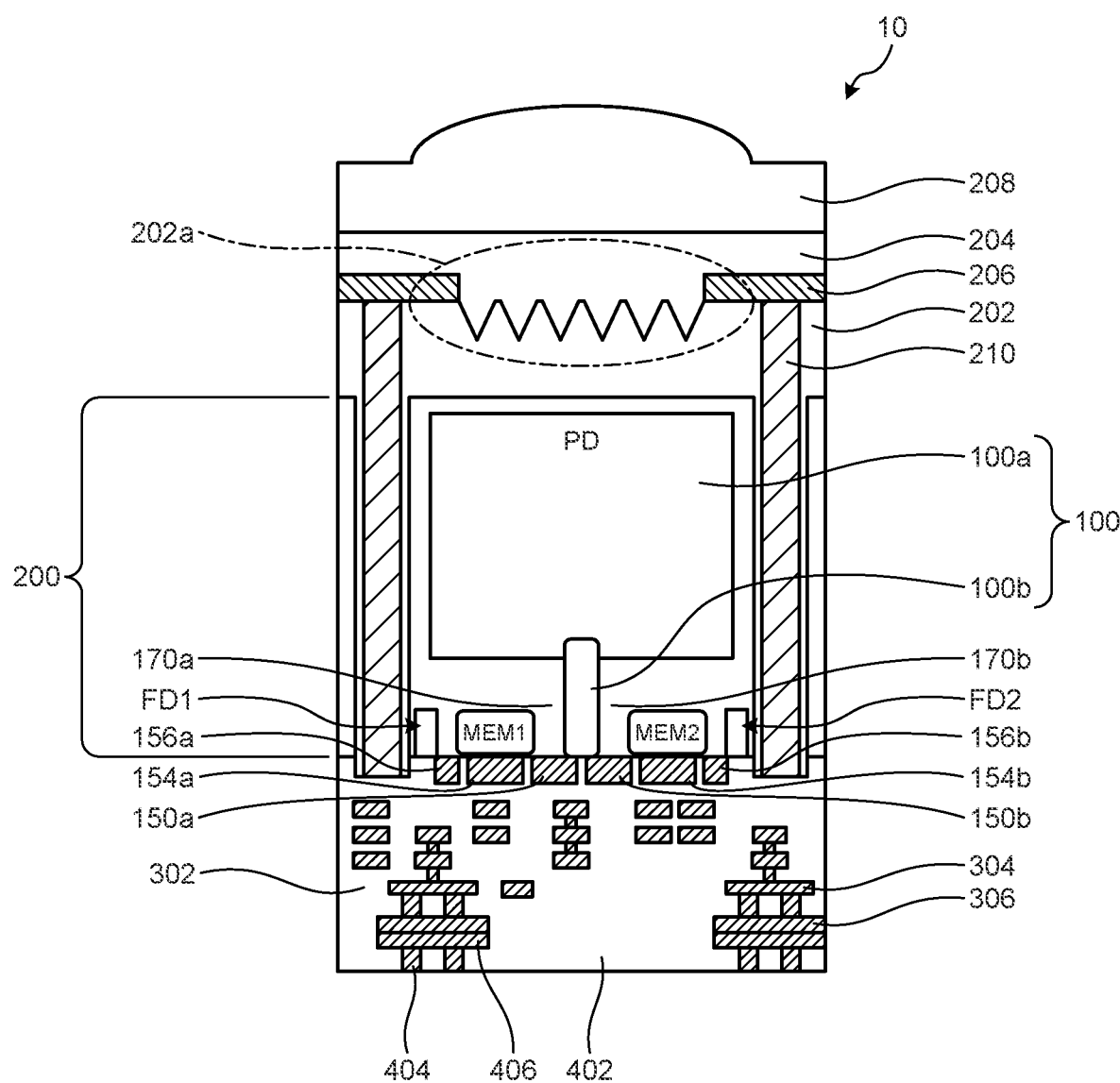
FIG. 15 is an explanatory diagram illustrating a cross-sectional configuration example of a light receiving element 10 according to a second variation example of the same embodiment.

Next, the second variation example will be described with reference to FIG. 15. FIG. 15 is an explanatory diagram illustrating a cross-sectional configuration example of a light receiving element 10 according to the second variation example of the present embodiment. Also in the present variation example, the light receiving element 10 includes charge accumulation units MEM1 and MEM2 each including a MOS capacitance. Furthermore, in the present variation example, as illustrated in FIG. 15, the light receiving element 10 has a moth-eye structure 202a provided on the back surface (surface opposite to the front surface) of the semiconductor substrate 200 and formed with fine unevenness. In detail, as illustrated in FIG. 15, the moth-eye structure 202a is configured by arranging a plurality of substantially quadrangular pyramids having apexes on the semiconductor substrate 200 side in a matrix form. In the present variation example, by providing the moth-eye structure 202a, it is possible to alleviate a rapid change in refractive index at the interface and to prevent reflection.

Third Variation Example

Figure 16:
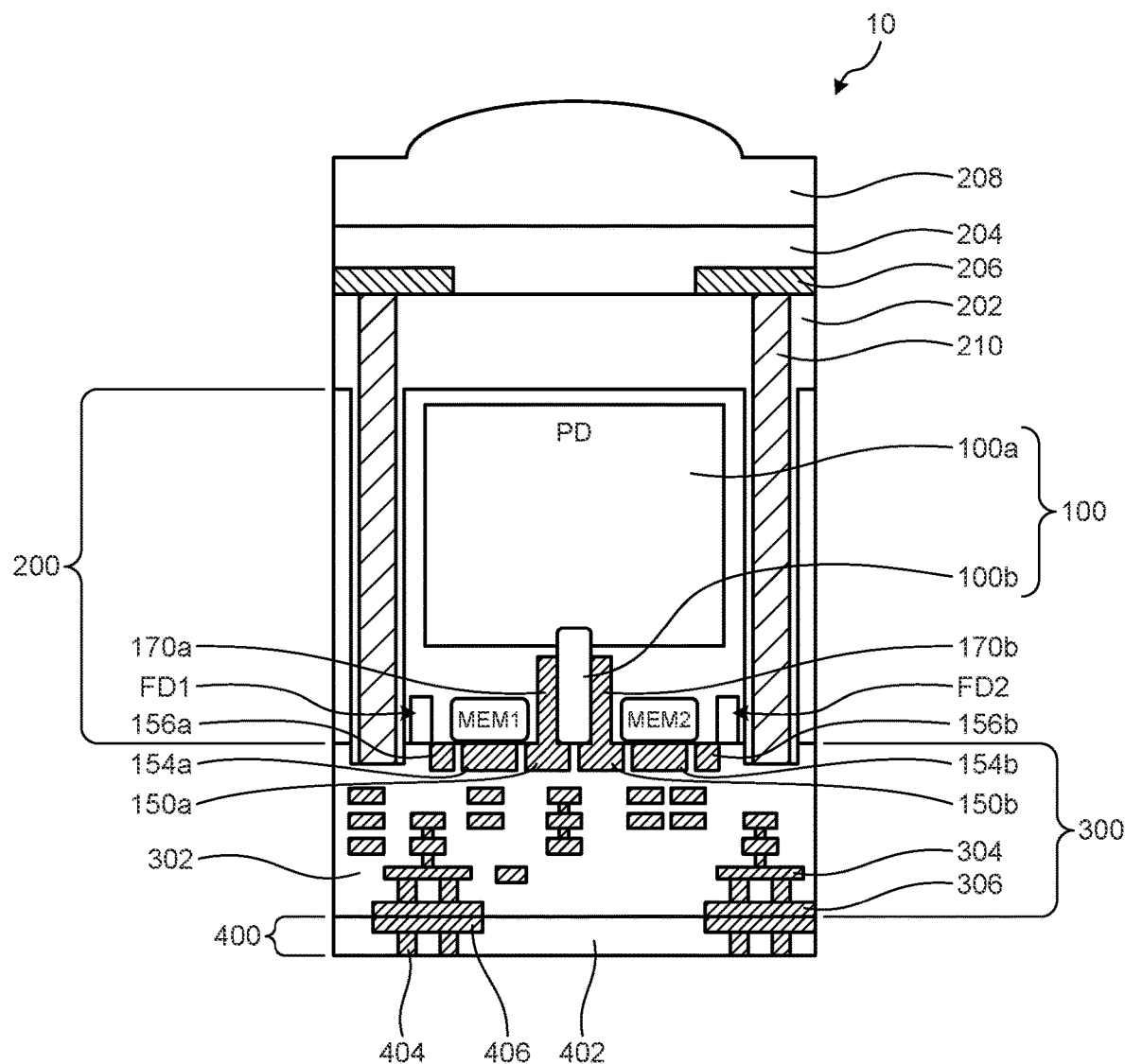
FIG. 16 is an explanatory diagram illustrating a cross-sectional configuration example of a light receiving element 10 according to a third variation example of the same embodiment.

Next, the third variation example will be described with reference to FIG. 16. FIG. 16 is an explanatory diagram illustrating a cross-sectional configuration example of the light receiving element 10 according to the third variation example of the present embodiment. Also in the present variation example, the light receiving element 10 includes charge accumulation units MEM1 and MEM2 each including a MOS capacitance. Furthermore, in the present variation example, as illustrated in FIG. 16, gate electrodes 150a and 150b of sorting transistors VG1 and VG2 have embedded gate portions 170a and 170b embedded in a semiconductor substrate 200. According to the present variation example, in the manner described above, the charge generated in a photodiode PD can be more efficiently transferred to the charge accumulation units MEM1 and MEM2.

Fourth Variation Example

Figure 17:
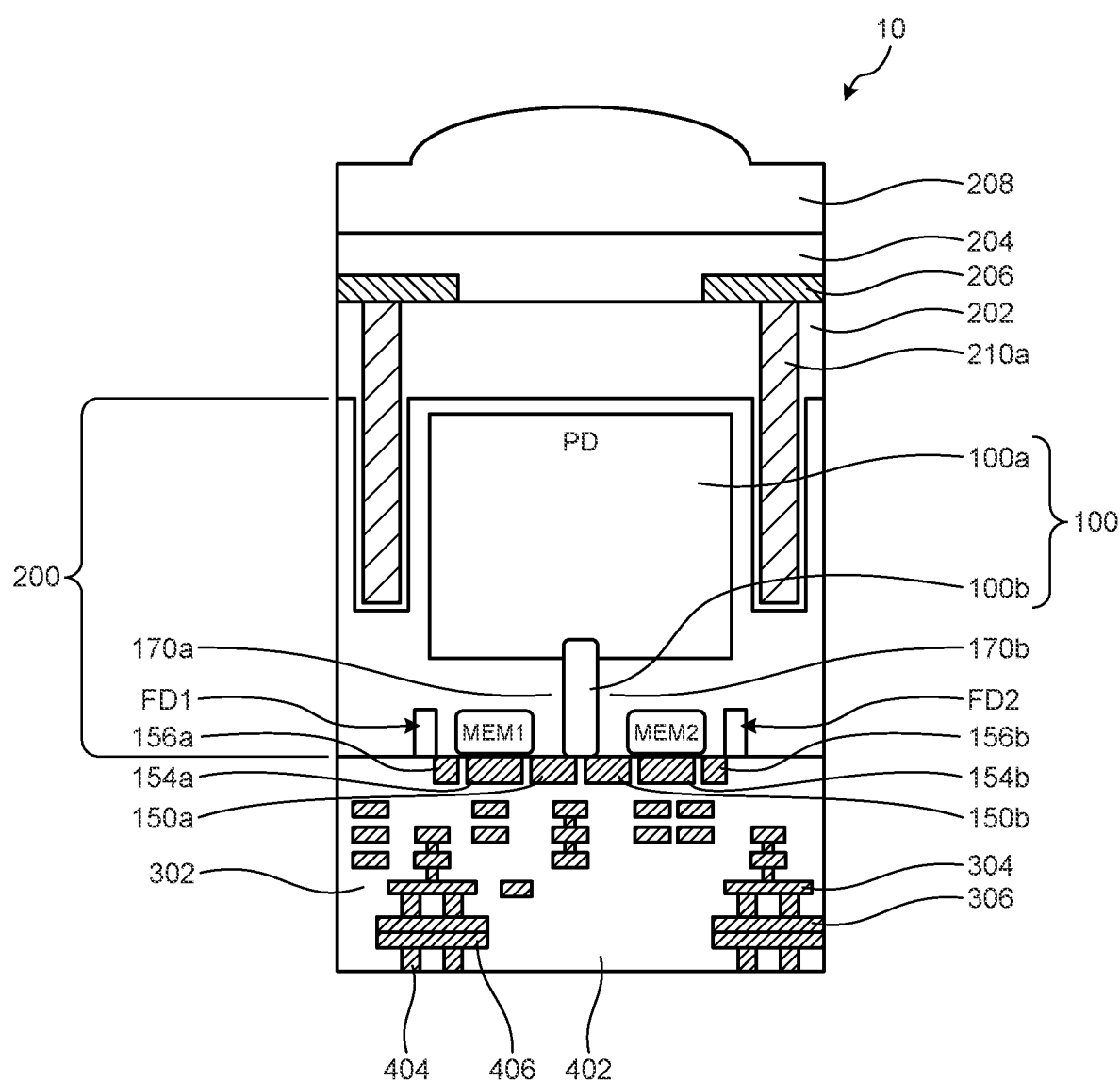
FIG. 17 is an explanatory diagram illustrating a cross-sectional configuration example of a light receiving element 10 according to a fourth variation example of the same embodiment.

Next, the fourth variation example will be described with reference to FIG. 17. FIG. 17 is an explanatory diagram illustrating a cross-sectional configuration example of the light receiving element 10 according to the fourth variation example of the present embodiment. Also in the present variation example, the light receiving element 10 includes charge accumulation units MEM1 and MEM2 each including a MOS capacitance. Furthermore, in the present variation example, as illustrated in FIG. 17, the light receiving element 10 includes a pixel isolation portion (second pixel isolation portion) 210a (deep trench isolation (DTI)) penetrating from the back surface (surface opposite to the front surface) of the semiconductor substrate 200 to the middle of the semiconductor substrate 200 along the thickness direction of the semiconductor substrate 200. With the pixel isolation portion 210a, it is possible to prevent incident light from entering an adjacent light receiving element 10.

Fifth Variation Example

Figure 18:
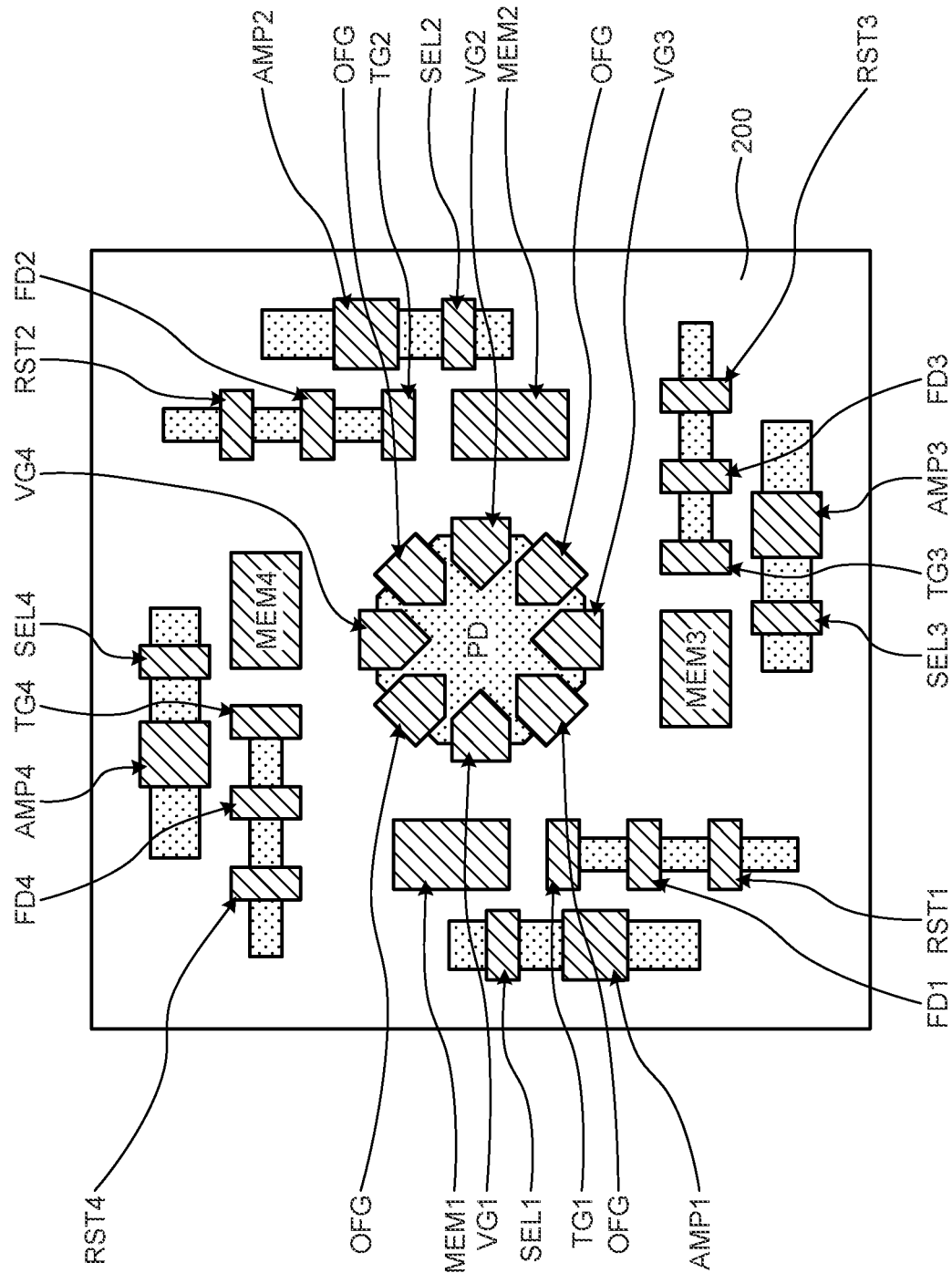
FIG. 18 is an explanatory diagram illustrating a planar formation example of a light receiving element 10 according to a fifth variation example of the same embodiment.

Next, the fifth variation example will be described with reference to FIG. 18. FIG. 18 is an explanatory diagram illustrating a cross-sectional configuration example of the light receiving element 10 according to the fifth variation example of the present embodiment. In the present variation example, as illustrated in FIG. 18, the light receiving element 10 may include a plurality of, in detail, four sorting transistors VG. Also in the present variation example, the light receiving element 10 includes charge accumulation units (third charge accumulation units) MEM1, MEM2, MEM3 and MEM4 each including a MOS capacitance.

7. SECOND EMBODIMENT

Further, in the first embodiment and the variation examples thereof described above, the insulating film (illustration omitted) of the charge accumulation units MEM1 and MEM2, the gate insulating film (illustration omitted) of the amplification transistors AMP1 and AMP2, and the like may be thinned. In this way, the capacitance of the charge accumulation units MEM1 and MEM2 can be increased without increasing the size. Furthermore, since the number of crystal defects in the gate insulating film decreases, the influence of crystal defects decreases due to an increase in transconductance gm of the transistor, or the interface state decreases due to a reduction in the heat treatment time or a reduction in the heat treatment temperature, random noise of the amplification transistors AMP1 and AMP2 can be reduced.

Figure 19:
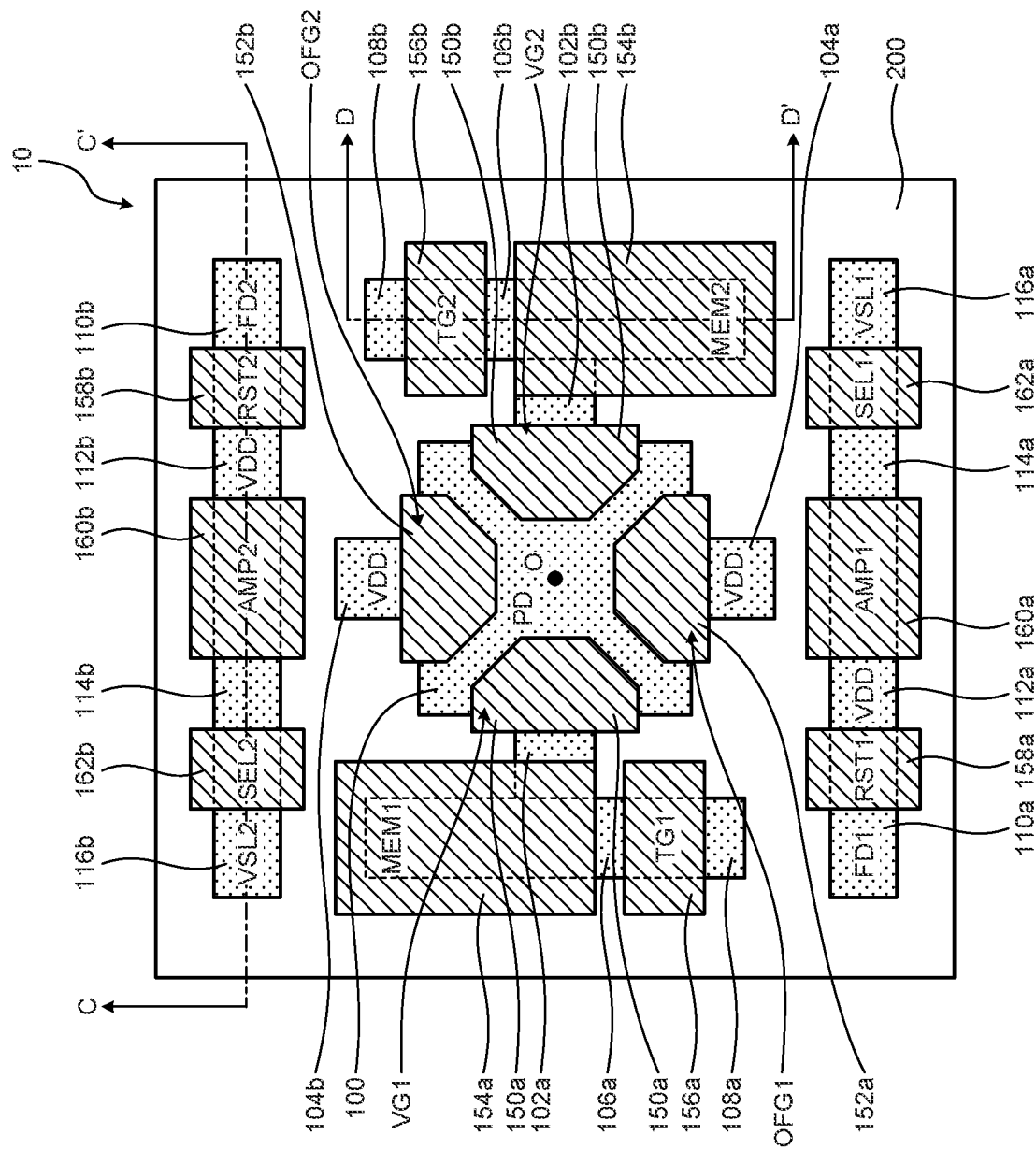
FIG. 19 is an explanatory diagram illustrating a planar configuration example of a light receiving element 10 according to a second embodiment of the present disclosure.
Figure 20A:
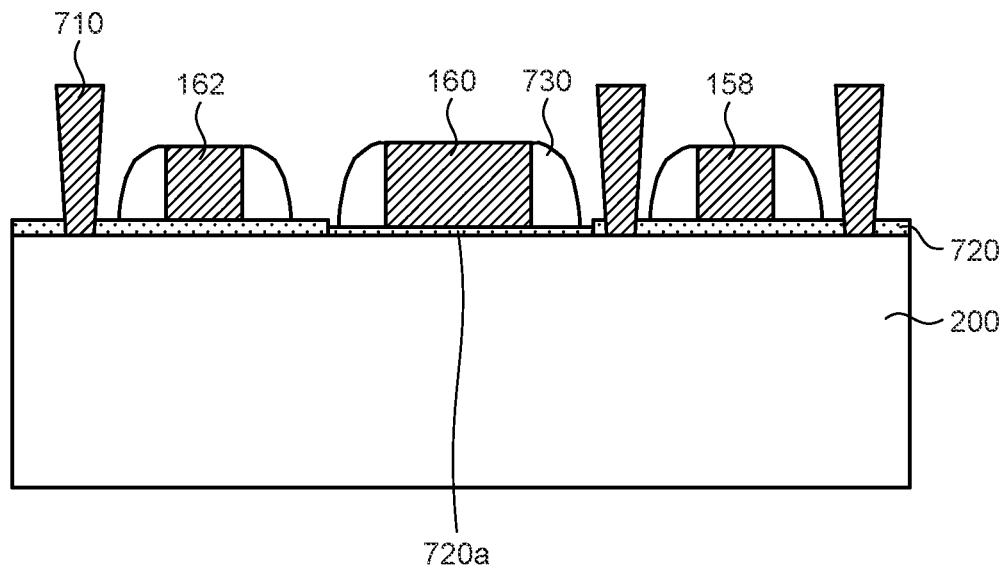
FIG. 20A is a cross-sectional diagram of the light receiving element 10 cut along line C-C' in FIG. 19.
Figure 20B:
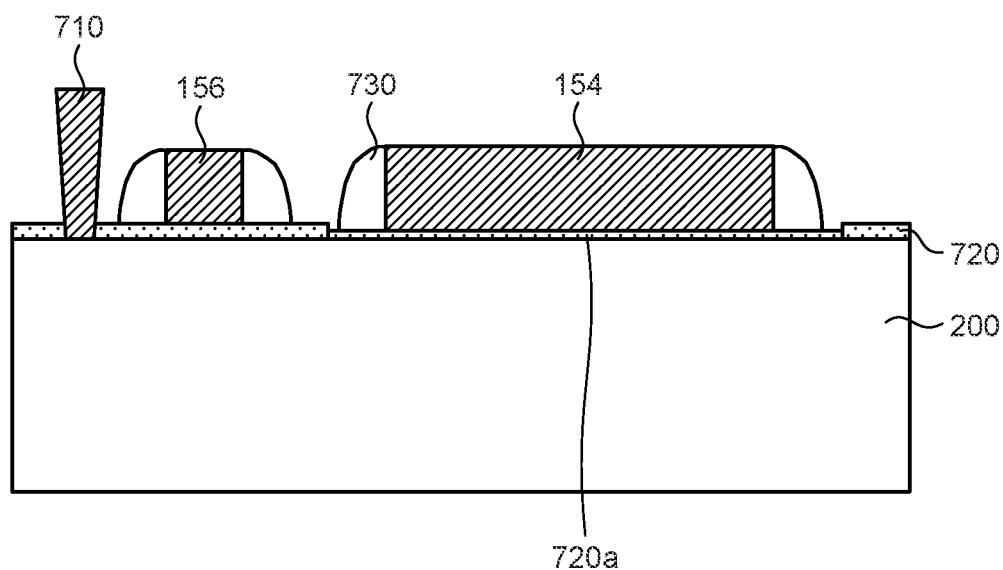
FIG. 20B is a cross-sectional diagram of the light receiving element 10 cut along line D-D' in FIG. 19.

Here, a third embodiment of the present disclosure for charge accumulation units MEM1 and MEM2 and amplification transistors AMP1 and AMP2 having a thinned insulating film will be described with reference to FIGS. 19, 20A, and 20B. Note that FIG. 19 is an explanatory diagram illustrating a planar configuration example of a light receiving element 10 according to the present embodiment, and is a diagram of the light receiving element 10 when viewed from above the front surface of a semiconductor substrate 200 similarly to the light receiving element 10 of the first embodiment. Further, FIG. 20A is a cross-sectional diagram of the light receiving element 10 cut along line C-C' in FIG. 19, and FIG. 20B is a cross-sectional diagram of the light receiving element 10 cut along line D-D' in FIG. 19. In detail, in FIGS. 20A and 20B, the upper side in the drawings is the front surface side of the semiconductor substrate 200, and the lower side in the drawings is the back surface side of the semiconductor substrate 200.

In detail, in the present embodiment, for example, as illustrated in FIG. 20A, an insulating film 720a of the amplification transistor AMP1 located below a gate electrode 160 covered with a sidewall 730 is made of, for example, an oxide film (third oxide film), and its film thickness is thinner than that of an insulating film 720 made of an oxide film (third oxide film) located below a gate electrode 158 of a reset transistor RST1 and a gate electrode 162 of a selection transistor SEL1.

Further, in the present embodiment, for example, as illustrated in FIG. 20B, an insulating film (insulating layer) 720a of the charge accumulation unit MEM1 located below an electrode 154 covered with a sidewall 730 is made of, for example, an oxide film (first oxide film), and its film thickness is thinner than that of an insulating film 720 made of an oxide film (second oxide film) located below a gate electrode 156 of a transfer transistor TG1.

Note that, in the present embodiment, the insulating film 720a located below the gate electrode 160 of the amplification transistor AMP1 and the insulating film 720a located below the electrode 154 of the charge accumulation unit MEM1 may be oxide films made of the same material and may have substantially the same film thickness.

More specifically, in the present embodiment, the insulating film 720a located below the gate electrode 160 of the amplification transistor AMP1 and the insulating film 720a located below the electrode 154 of the charge accumulation unit MEM1 are made of an oxide film of silicon oxide ($SiO_2$), silicon nitride (SiN), or the like. Further, in the present embodiment, in view of the effect of reducing random noise and an increase in power consumption due to increases in leakage current due to a reduction in thickness, the film thickness of the insulating film 720a located below the gate electrode 160 of the amplification transistor AMP1 and the insulating film 720a located below the electrode 154 of the charge accumulation unit MEM1 is preferably about half of the film thickness of the insulating film 720 located below the gate electrodes 156, 158, and 162 of the other elements (transfer transistor TG, reset transistor RST, and selection transistor SEL), and more preferably, for example, 1.0 nm or more and 5.0 nm or less.

Furthermore, in the present embodiment, the insulating film 720a located below the gate electrode 160 of the amplification transistor AMP1 and the insulating film 720a located below the electrode 154 of the charge accumulation unit MEM1 are preferably wider than the gate electrode 160 and the electrode 154 to the extent not to interfere with adjacent elements when viewed from above the semiconductor substrate 200.

Note that, in the present embodiment, it is not limited to thinning only the insulating film 720a of the charge accumulation units MEM1 and MEM2 and the gate insulating film 720a of the amplification transistors AMP1 and AMP2. In the present embodiment, only the insulating film 720a of the charge accumulation units MEM1 and MEM2 may be thinned, and the insulating film 720 in contact with the gate electrodes 150, 152, 154, 156, 158, 160, and 162 and the electrode 154 of the elements (charge accumulation unit MEM, transfer transistor TG, sorting transistor VG, charge discharge transistor OFG, amplification transistor AMP, reset transistor RST, and selection transistor SEL) on the light receiving element 10 may be thinned.

As described above, according to the present embodiment, by thinning the insulating film 720a of the charge accumulation unit MEM, the gate insulating film 720a of the amplification transistor AMP, and the like, the capacitance of the charge accumulation unit MEM can be increased without increasing the size, and random noise of the transistor can be reduced. Thus, according to the present embodiment, by combining with the configuration according to the above-described first embodiment, it is possible to provide the light receiving element 10 and the distance measurement module 1 capable of further reducing the influence of kTC noise while ensuring a wider dynamic range. Note that the present embodiment can be carried out in combination with the first embodiment and the variation examples thereof described above.

8. THIRD EMBODIMENT

Incidentally, in the second embodiment described above, the insulating film 720a of the charge accumulation unit MEM, the gate insulating film 720a of the amplification transistor AMP, and the like are thinned to increase the capacitance of the charge accumulation unit MEM and reduce the random noise of the amplification transistor AMP. However, in a case where the thinning of the gate insulating film 720a is advanced, although the above-described effect can be obtained, the leakage current increases, and thus there is a limit to the thinning. Therefore, the present inventors have conceived that a high dielectric film having a high relative dielectric constant capable of increasing the capacitance of the charge accumulation unit MEM as compared with the above-described oxide film even with the same film thickness is used instead of the insulating film 720a described above. By using a high dielectric film as the insulating film 720a described above, it is possible to achieve both an increase in capacitance of the charge accumulation unit MEM and a reduction in random noise of the amplification transistor AMP while avoiding an increase in leakage current even when the film thickness is reduced.

Figure 21:
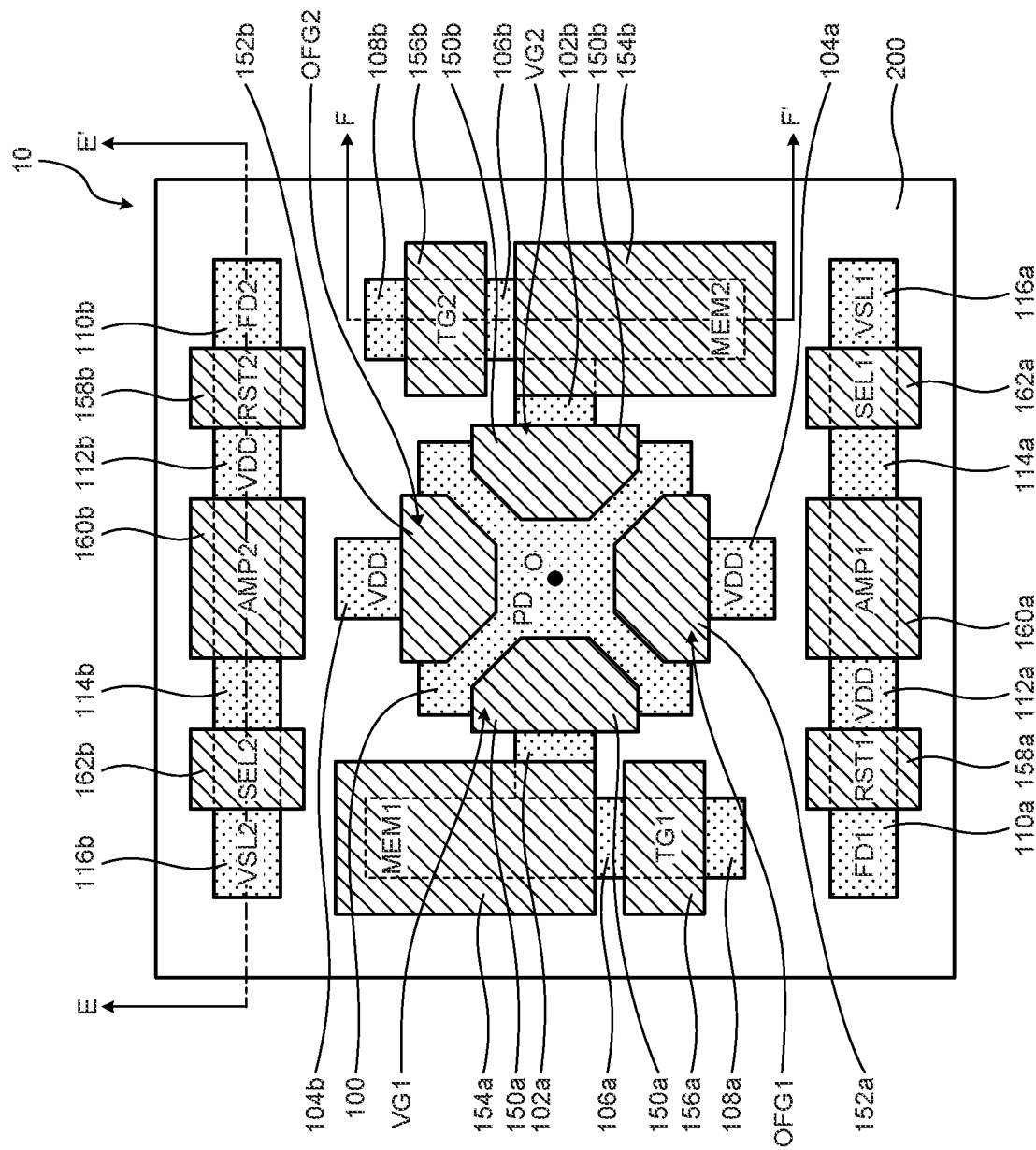
FIG. 21 is an explanatory diagram illustrating a planar configuration example of a light receiving element 10 according to a third embodiment of the present disclosure.
Figure 22A:
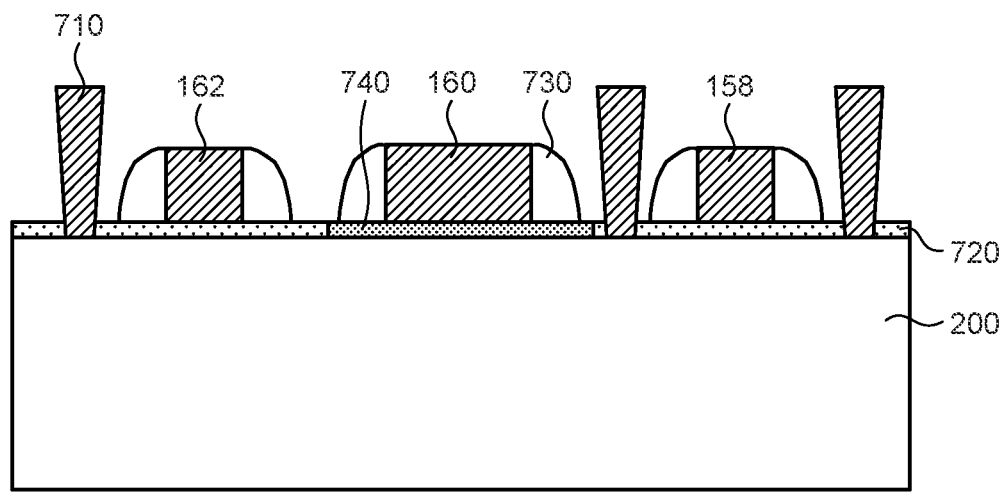
FIG. 22A is a cross-sectional diagram of the light receiving element 10 cut along line E-E' in FIG. 21.
Figure 22B:
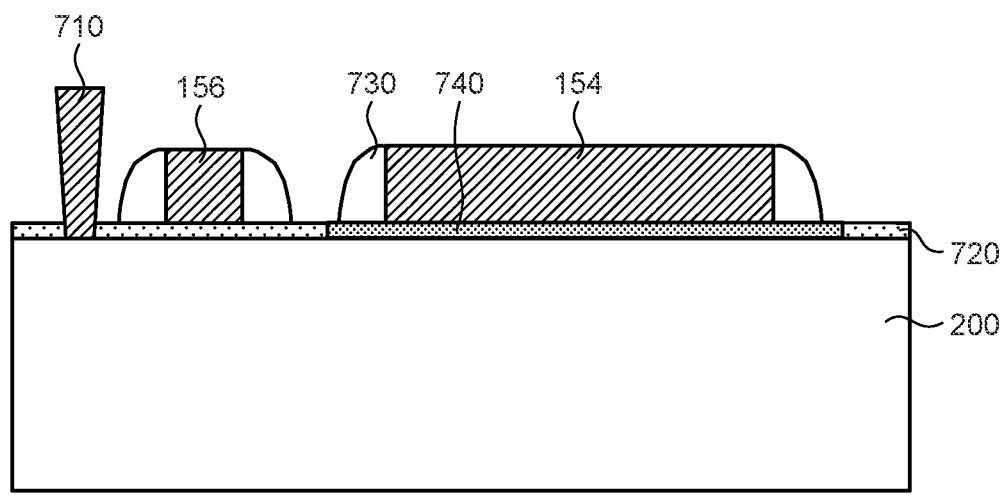
FIG. 22B is a cross-sectional diagram of the light receiving element 10 cut along line F-F' in FIG. 21.
Figure 24:
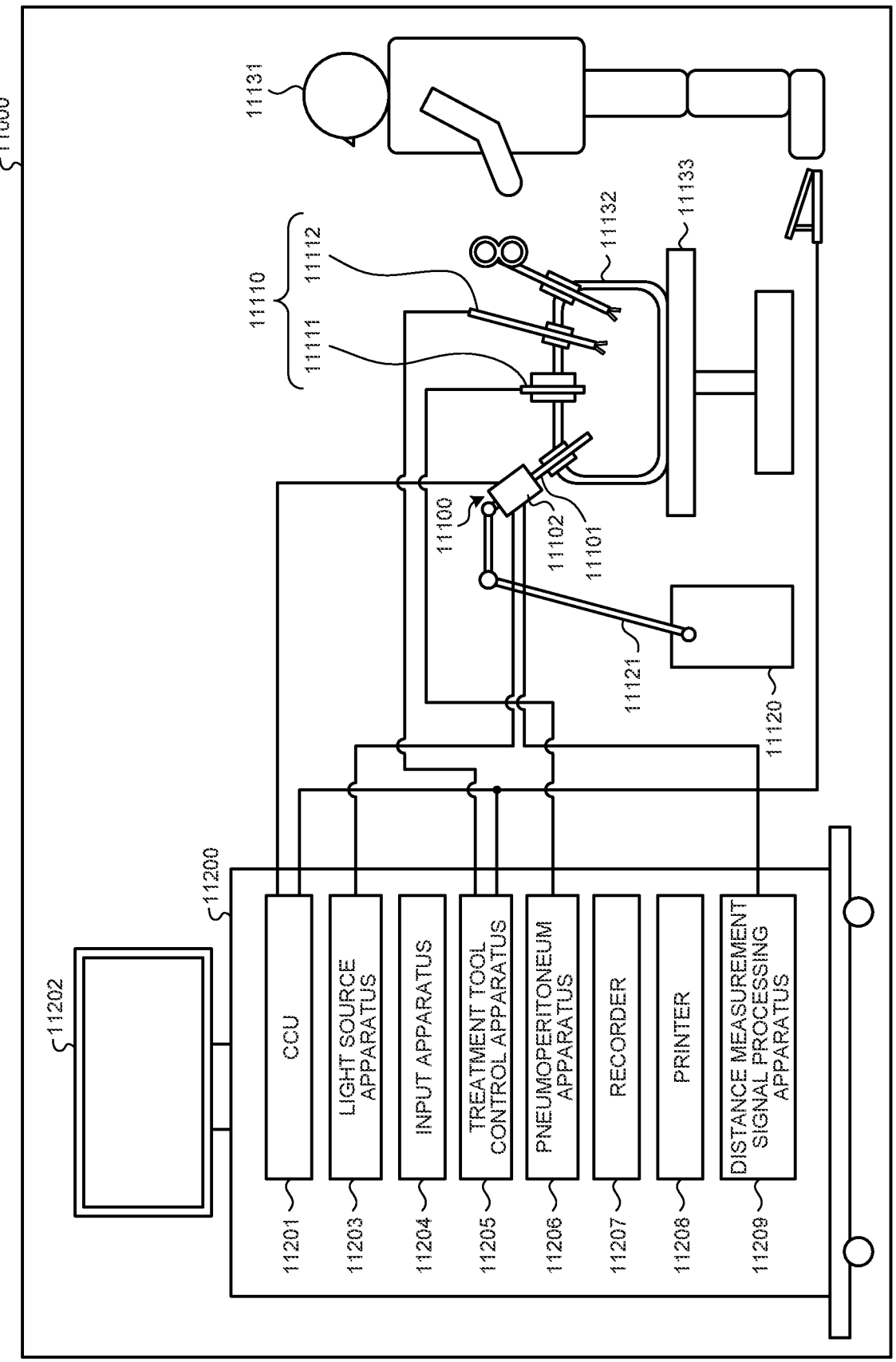
FIG. 24 is a diagram illustrating an example of a schematic configuration of an endoscopic surgery system.

Here, a fourth embodiment of the present disclosure for charge accumulation units MEM1 and MEM2 and amplification transistors AMP1 and AMP2 having an insulating film made of a high dielectric film will be described with reference to FIGS. 21, 22A, and 22B. Note that FIG. 21 is an explanatory diagram illustrating a planar configuration example of a light receiving element 10 according to the present embodiment, and is a diagram of the light receiving element 10 when viewed from above the front surface of a semiconductor substrate 200 similarly to the light receiving element 10 of the first embodiment. Further, FIG. 22A is a cross-sectional diagram of the light receiving element 10 cut along line E-E' in FIG. 24, and FIG. 22B is a cross-sectional diagram of the light receiving element 10 cut along line F-F' in FIG. 24. In detail, in FIGS. 22A and 22B, the upper side in the drawings is the front surface side of the semiconductor substrate 200, and the lower side in the drawings is the back surface side of the semiconductor substrate 200.

In detail, in the present embodiment, for example, as illustrated in FIG. 22A, an insulating film (third insulating layer) 740 of the amplification transistor AMP1 located below a gate electrode 160 covered with a sidewall 730 is made of a high dielectric film. Then, the relative dielectric constant of the insulating film 740 is higher than that of an insulating film (third insulating layer) 720 located below a gate electrode 158 of a reset transistor RST1 and a gate electrode 162 of a selection transistor SEL1.

Further, in the present embodiment, for example, as illustrated in FIG. 22B, an insulating film (first insulating layer) 740 of the charge accumulation unit MEM1 located below an electrode 154 covered a sidewall 730 is made of a high dielectric film. The relative dielectric constant of the insulating film 740 is higher than that of an insulating film (second insulating layer) 720 located below a gate electrode 156 of a transfer transistor TG1.

Note that, in the present embodiment, the insulating film 740 located below the gate electrode 160 of the amplification transistor AMP1 and the insulating film 740 located below the electrode 154 of the charge accumulation unit MEM1 may be made of the same material.

More specifically, in the present embodiment, the high dielectric film is a material having a relative dielectric constant higher than the relative dielectric constant (3.9) of silicon oxide ($SiO_2$), and is preferably a material having a relative dielectric constant of 4 or more. In the present embodiment, for example, the high dielectric film is a metal oxide film, and can be formed of a material such as $Al_2O_3$, HfSiON, $Y_2O_3$, $Ta_2O_5$, $La_2O_3$, $TiO_2$, $HfO_2$, $ZrO_2$, or $HfZrO_2$.

When the high dielectric film described above is used as the insulating film 740, a metal material such as TiN, TaN, or NiSi may be used as a material for forming the gate electrodes 150, 152, 154, 156, 158, 160, and 162 in order to adjust Vth (threshold voltage).

Furthermore, in the present embodiment, the insulating film 740 located below the gate electrode 160 of the amplification transistor AMP1 and the insulating film 740 located below the electrode 154 of the charge accumulation unit MEM1 are preferably wider than the gate electrode 160 and the electrode 154 to the extent not to interfere with adjacent elements when viewed from above the semiconductor substrate 200.

Note that, in the present embodiment, it is not limited to form only the insulating film 740 of the charge accumulation units MEM1 and MEM2 and the gate insulating film 740 of the amplification transistors AMP1 and AMP2 by using a high dielectric film. In the present embodiment, only the insulating film 740 of the charge accumulation units MEM1 and MEM2 may be formed of a high dielectric film, and the insulating film 720 in contact with the gate electrodes 150, 152, 154, 156, 158, 160, and 162 and the electrode 154 of the elements (charge accumulation unit MEM, transfer transistor TG, sorting transistor VG, charge discharge transistor OFG, amplification transistor AMP, reset transistor RST, and selection transistor SEL) on the light receiving element 10 may be formed of a high dielectric film.

As described above, according to the present embodiment, by forming the insulating film 740 of the charge accumulation unit MEM, the gate insulating film 740 of the amplification transistor AMP, and the like by using a high dielectric film, it is possible to achieve both an increase in capacitance of the charge accumulation unit MEM and a reduction in random noise of the amplification transistor AMP without reducing the film thickness as compared with the case of using $SiO_2$. Thus, according to the present embodiment, by combining with the configuration according to the above-described first embodiment, it is possible to provide the light receiving element 10 and the distance measurement module 1 capable of further reducing the influence of kTC noise while ensuring a wider dynamic range. Note that the present embodiment can be carried out in combination with the first embodiment and the variation examples thereof described above.

9. CONCLUSION

As described above, according to the embodiments and the variation examples of the present disclosure, it is possible to provide the light receiving element 10 and the distance measurement module 1 capable of reducing the influence of kTC noise while ensuring a wide dynamic range.

Although the present disclosure has been described with reference to the embodiments, the variation examples, examples of application, and application examples thereof, the present disclosure is not limited to the embodiments and the like described above, and various variations can be made. Note that the effects described in the present specification are merely exemplary. The effects of the present disclosure are not limited to those described in the present specification. The present disclosure may have any other effects than those described in the present specification.

Note that, in the embodiments and the variation examples of the present disclosure described above, the conductivity type of each semiconductor region described above may be reversed, and for example, the present embodiments and the variation examples can be applied to an element using holes as charges instead of electrons.

Further, in the embodiments and the variation examples of the present disclosure described above, the semiconductor substrate may not necessarily be a silicon substrate, but may be another substrate (for example, a silicon on insulator (SOI) substrate, a SiGe substrate, or the like). Further, the semiconductor substrate described above may have a semiconductor structure or the like formed on such various substrates.

Further, in the embodiments and the variation examples of the present disclosure described above, the light receiving element 10 may be formed on one chip together with the irradiation unit, the processing circuit, and the like, or may be provided in one package, and is not particularly limited.

Note that, in the embodiments and the variation examples of the present disclosure, examples of a method of forming each layer, each film, each element, and the like described above include a physical vapor deposition (PVD) method, a chemical vapor deposition (CVD) method, and the like. Examples of the PVD method can include vacuum deposition processes using resistance heating or radio-frequency heating, electron beam (EB) deposition processes, various sputtering processes (magnetron sputtering processes, radio frequency-direct current (RF-DC) coupled bias sputtering processes, electron cyclotron resonance (ECR) sputtering processes, facing target sputtering processes, radio-frequency sputtering processes), ion plating processes, laser ablation processes, molecular beam epitaxy (MBE) processes, and laser transfer processes. Further, examples of the CVD method include plasma CVD processes, thermal CVD processes, metal organic (MO) CVD processes, and photo-CVD processes. Furthermore, other methods include various coating methods such as an electrolytic plating method, an electroless plating method, a spin coat method; a dipping method; a cast method; a microcontact printing method; a drop cast method; various printing methods such as a screen printing method, an ink jet printing method, an offset printing method, a gravure printing method, and a flexo printing method; a stamp method; a spray method; an air doctor coater method, a blade coater method, a rod coater method, a knife coater method, a squeeze coater method, a reverse roll coater method, a transfer roll coater method, a gravure coater method, a kiss coater method, a cast coater method, a spray coater method, a slit orifice coater method, and a calendar coater method. Further, examples of patterning methods of each layer include shadow-masking, laser transfer, chemical etching such as photolithography, physical etching by ultraviolet rays or laser beams or the like. In addition, examples of a planarization technique include a chemical mechanical polishing (CMP) method, a laser planarization method, reflow method, or the like. That is, the elements according to the embodiments and the variation examples of the present disclosure can be easily and inexpensively manufactured using an existing semiconductor apparatus manufacturing process.

10. CONFIGURATION EXAMPLE OF ELECTRONIC DEVICE

Figure 23:
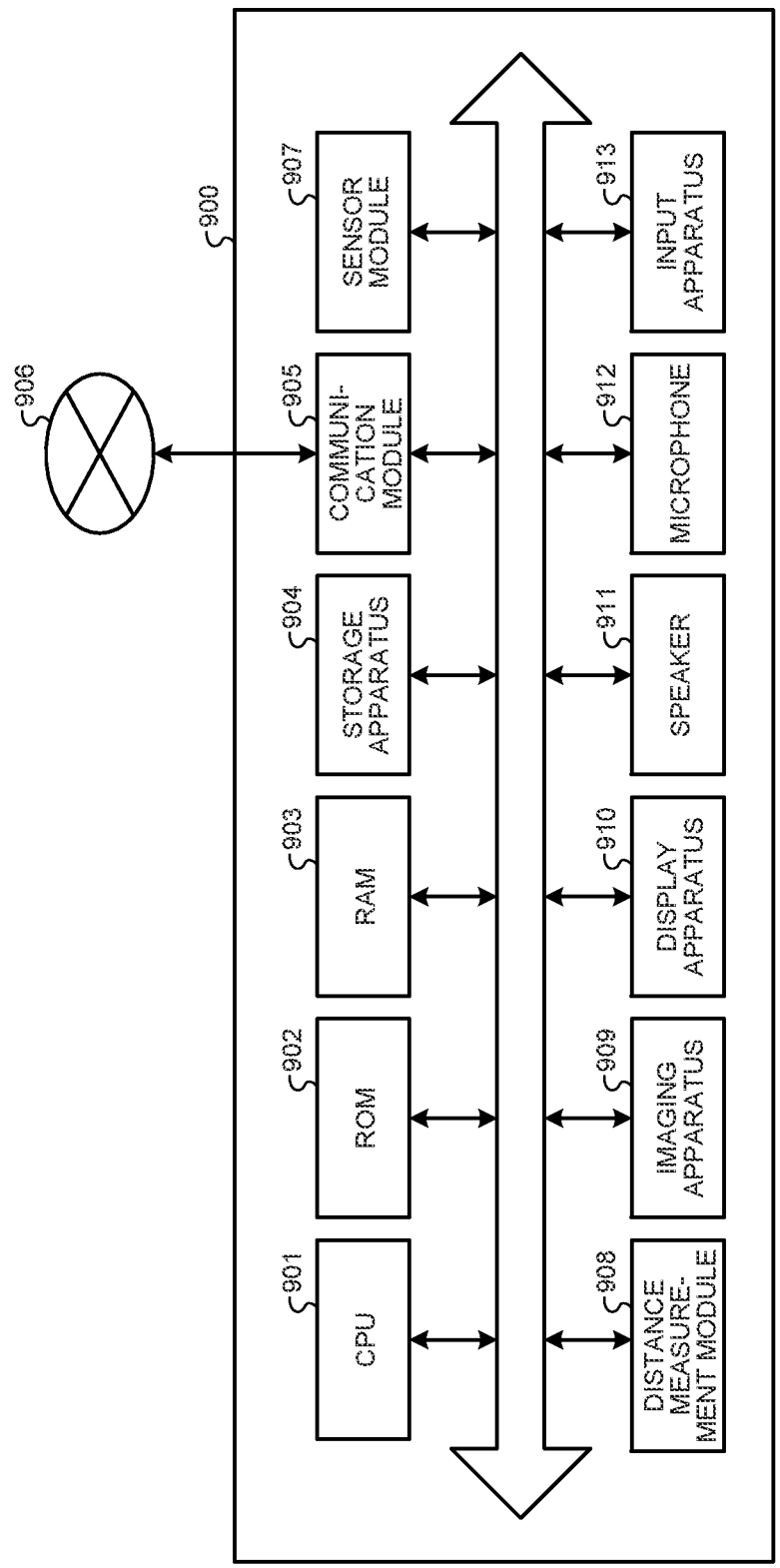
FIG. 23 is a block diagram illustrating a configuration example of a smartphone 900, which is an electronic device, to which the distance measurement module 1 according to the embodiment of the present disclosure is applied.

Note that the light receiving element 10 can be applied not only to the distance measurement module 1 as described above but also to various electronic devices such as, for example, a camera having a distance measurement function and a smartphone having a distance measurement function. Therefore, a configuration example of the smartphone 900, which is an electronic device to which the present technology is applied, will be described with reference to FIG. 23. FIG. 23 is a block diagram illustrating a configuration example of the smartphone 900, which is an electronic device to which the distance measurement module 1 according to the embodiment of the present disclosure is applied.

As illustrated in FIG. 23, the smartphone 900 includes a central processing unit (CPU) 901, a read only memory (ROM) 902, and a random access memory (RAM) 903. Further, the smartphone 900 includes a storage apparatus 904, a communication module 905, and a sensor module 907. Furthermore, the smartphone 900 includes a distance measurement module 908 to which the above-described distance measurement module 1 can be applied, and includes, in addition, an imaging apparatus 909, a display apparatus 910, a speaker 911, a microphone 912, an input apparatus 913, and a bus 914. Further, the smartphone 900 may include a processing circuit such as a digital signal processor (DSP) instead of or in addition to the CPU 901.

The CPU 901 functions as an arithmetic processing apparatus and a control apparatus, and controls the entire operation or part of the operation of the smartphone 900 according to various programs recorded in the ROM 902, the RAM 903, the storage apparatus 904, or the like. The ROM 902 stores a program, arithmetic parameters, and the like used by the CPU 901. The RAM 903 primarily stores the programs used in the execution of the CPU 901 and the parameters that appropriately vary in this execution, and the like. The CPU 901, the ROM 902, and the RAM 903 are connected to one another by the bus 914. Further, the storage apparatus 904 is a data storage apparatus configured as an example of a storage unit of the smartphone 900. The storage apparatus 904 includes, for example, a magnetic storage device such as a hard disk drive (HDD), a semiconductor storage device, an optical storage device, or the like. The storage apparatus 904 stores programs and various data executed by the CPU 901, various data acquired from the outside, and the like.

The communication module 905 is, for example, a communication interface including a communication device through which connection to a communication network 906 is established, and the like. The communication module 905 can be, for example, a communication card for a wired or wireless local area network (LAN), a Bluetooth (registered trademark), or a wireless USB (WUSB). Further, the communication module 905 may be a router for optical communication, a router for asymmetric digital subscriber line (ADSL), a modem for various types of communication, or the like. The communication module 905 transmits and receives a signal or the like to and from the Internet and other communication devices using a predetermined protocol such as TCP/IP. Further, the communication network 906 connected to the communication module 905 is a network connected by wire or wirelessly, and is, for example, the Internet, a home LAN, infrared communication, satellite communication, or the like.

The sensor module 907 includes, for example, various sensors such as a motion sensor (for example, an acceleration sensor, a gyro sensor, a geomagnetic sensor, or the like), a biological information sensor (for example, a pulse sensor, a blood pressure sensor, a fingerprint sensor, or the like), or a position sensor (for example, a global navigation satellite system (GNSS) receiver or the like).

The distance measurement module 908 is provided on the surface of the smartphone 900, and can acquire, for example, an uneven shape or movement of the user's fingertip, palm, face, or the like facing the surface as a distance measurement result. Such a distance measurement result can be used for authentication of the user and recognition of a gesture of the user. Further, the distance measurement module 908 can also acquire, for example, a distance from the smartphone 900 to the object 800 or three-dimensional shape data of the surface of the object 800.

The imaging apparatus 909 is provided on the surface of the smartphone 900, and can capture an image of the object 800 or the like located around the smartphone 900. In detail, the imaging apparatus 909 can include an imaging element (illustration omitted) such as a complementary MOS (CMOS) image sensor, and a signal processing circuit (illustration omitted) that performs imaging signal processing on a signal photoelectrically converted by the imaging element. Furthermore, the imaging apparatus 909 can further include an optical system mechanism (illustration omitted) including an imaging lens, a diaphragm mechanism, a zoom lens, a focusing lens, and the like, and a drive system mechanism (illustration omitted) that controls the operation of the optical system mechanism described above. Then, the imaging element described above collects incident light from the object 800 as an optical image, and the signal processing circuit described above photoelectrically converts the formed optical image in units of pixels, reads a signal of each pixel as an imaging signal, and performs image processing to acquire a captured image.

The display apparatus 910 is provided on the surface of the smartphone 900, and can be, for example, a display apparatus such as a liquid crystal display (LCD) or an organic electro luminescence (EL) display. The display apparatus 910 can display an operation screen, a captured image acquired by the above-described imaging apparatus 909, and the like.

The speaker 911 can output, for example, a call voice, a voice accompanying content displayed by the above-described display apparatus 910, and the like to the user.

The microphone 912 can collect, for example, a call voice of the user, a voice including a command to activate a function of the smartphone 900, and a voice in a surrounding environment of the smartphone 900.

The input apparatus 913 is, for example, an apparatus operated by the user such as a button, a keyboard, a touch panel, a mouse, or the like. The input apparatus 913 includes an input control circuit that generates an input signal on the basis of information input by the user and outputs the input signal to the CPU 901. The user can input various types of data or instruct a processing operation to the smartphone 900 by operating the input apparatus 913.

The configurve. Each of the components described above may include a geation example of the smartphone 900 has been described aboneral-purpose member, or may include hardware specialized in the function of each component. Such a configuration can be appropriately changed depending on the technical level at the time of implementation.

11. APPLICATION EXAMPLE TO ENDOSCOPIC SURGERY SYSTEM

The technology according to the present disclosure (the present technology) can be applied to various products. For example, the technology according to the present disclosure may be applied to an endoscopic surgery system.

FIG. 24 is a diagram illustrating an example of a schematic configuration of an endoscopic surgery system to which the technology according to the present disclosure (the present technology) can be applied.

In FIG. 24, a state is illustrated in which a surgeon (medical doctor) 11131 is using an endoscopic surgery system 11000 to perform surgery for a patient 11132 on a patient bed 11133. As illustrated, the endoscopic surgery system 11000 includes an endoscope 11100, other surgical tools 11110 such as a pneumoperitoneum tube 11111 and an energy treatment tool 11112, a supporting arm apparatus 11120 that supports the endoscope 11100, and a cart 11200 on which various apparatuses for endoscopic surgery are mounted.

The endoscope 11100 includes a lens barrel 11101 having a region of a predetermined length from a distal end to be inserted into a body cavity of the patient 11132, and a camera head 11102 connected to a proximal end of the lens barrel 11101. In the illustrated example, the endoscope 11100 is illustrated that is configured as a rigid endoscope having the lens barrel 11101 of a hard type, but the endoscope 11100 may otherwise be configured as a flexible endoscope having the lens barrel of a flexible type.

The lens barrel 11101 has, at a distal end, an opening in which an objective lens is fitted. A light source apparatus 11203 is connected to the endoscope 11100 such that light generated by the light source apparatus 11203 is introduced to the distal end of the lens barrel by a lightguide extending in the lens barrel 11101 and is emitted toward an observation target in the body cavity of the patient 11132 through the objective lens. Note that the endoscope 11100 may be a forward-viewing endoscope or may be an oblique-viewing endoscope or a side-viewing endoscope. Furthermore, the irradiation unit 20 and the light receiving unit 30 of the distance measurement module 1 according to the embodiment of the present disclosure may be incorporated in the distal end of the lens barrel 11101. By mounting a part of such a distance measurement module 1, it is possible to further improve the accuracy of the surgery by referring to the distance information by the distance measurement module 1 as well as the surgery visually performed by the doctor.

Figure 25:
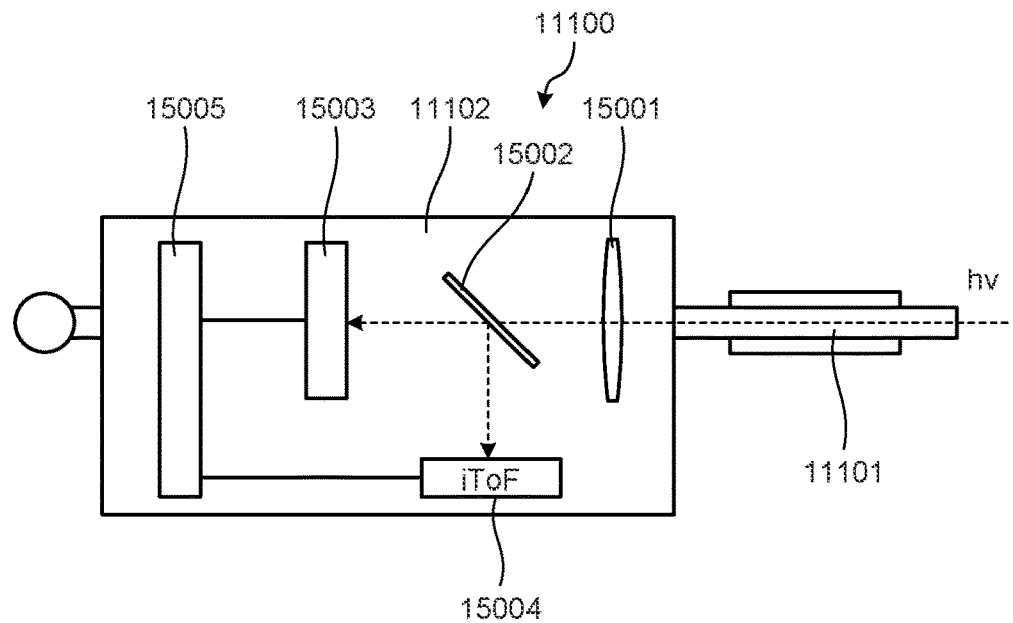
FIG. 25 is a diagram illustrating an example of a configuration of an endoscope.

For example, as in the configuration of FIG. 25 illustrating an example of the configuration of the endoscope 11100, an iToF sensor 15004, which is the irradiation unit 20 and the light receiving unit 30 of the distance measurement module 1 according to the embodiment of the present disclosure, is provided in the camera head 11102. In detail, reflected light (observation light) from the observation target passes through the lens barrel 11101, is condensed by a lens 15001 in the camera head 11102, is reflected by a half mirror 15002, and is received by the iToF sensor 15004. Furthermore, the observation light is photoelectrically converted by the iToF sensor 15004, an electric signal corresponding to the observation light is generated and stored in a memory 15005, and then transmitted to a distance measurement signal processing apparatus 11209 described below.

Furthermore, as illustrated in FIG. 25, an imaging element 15003 is provided in the camera head 11102, and reflected light (observation light) from the observation target passes through the lens barrel 11101, is condensed by the lens 15001, is reflected by the half mirror 15002, and is received by the imaging element 15003. The observation light is photoelectrically converted by the imaging element 15003, and an electric signal corresponding to the observation light, that is, an image signal corresponding to the observation image is generated. The image signal is once stored in the memory 15005 and then transmitted as RAW data to a camera control unit (CCU) 11201.

The CCU 11201 includes a central processing unit (CPU), a graphics processing unit (GPU) or the like and integrally controls operation of the endoscope 11100 and a display apparatus 11202. Furthermore, the CCU 11201 receives an image signal from the camera head 11102 and performs, for the image signal, various image processing for displaying an image based on the image signal such as, for example, development processing (demosaic processing).

The display apparatus 11202 displays an image based on the image signal, for which the image processing has been performed by the CCU 11201, under the control of the CCU 11201.

The light source apparatus 11203 includes a light source such as, for example, a light emitting diode (LED) and supplies irradiation light upon imaging of a surgical region or the like to the endoscope 11100.

An input apparatus 11204 is an input interface for the endoscopic surgery system 11000. A user can perform inputting of various kinds of information or instruction inputting to the endoscopic surgery system 11000 through the input apparatus 11204. For example, the user inputs an instruction or a like to change imaging conditions (type of irradiation light, magnification, focal distance or the like) by the endoscope 11100.

A treatment tool control apparatus 11205 controls driving of the energy treatment tool 11112 for cautery or incision of a tissue, sealing of a blood vessel, or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph. The distance measurement signal processing apparatus 11209 is an apparatus that is provided with the control unit 40 and the processing unit 60 of the distance measurement module 1 according to the embodiment of the present disclosure and can acquire distance information.

Note that the light source apparatus 11203 that supplies irradiation light when a surgical region is to be imaged to the endoscope 11100 may include a white light source including, for example, an LED, a laser light source or a combination thereof. When a white light source includes a combination of RGB laser light sources, since the output intensity and the output timing can be controlled with high accuracy for each color (each wavelength), adjustment of the white balance of a captured image can be performed by the light source apparatus 11203. Further, in this case, when laser beams from the respective RGB laser light sources are emitted time-divisionally to an observation target and driving of the imaging element of the camera head 11102 is controlled in synchronism with the irradiation timings, images corresponding to RGB can also be captured time-divisionally. According to this method, a color image can be obtained even when color filters are not provided for the imaging element.

Further, the driving of the light source apparatus 11203 may be controlled such that the intensity of light to be outputted is changed for each predetermined time. By controlling driving of the imaging element of the camera head 11102 in synchronism with the timing of the change in the intensity of light to acquire images time-divisionally and synthesizing the images, an image of a high dynamic range free of underexposed blocked up shadows and overexposed highlights can be generated.

Further, the light source apparatus 11203 may be configured to be capable of supplying light of a predetermined wavelength band corresponding to special light observation. In special light observation, for example, by utilizing the wavelength dependency of absorption of light in a body tissue to emit light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by emission of excitation light may be performed. In fluorescent observation, it is possible to perform observation of fluorescent light from a body tissue by emitting excitation light to the body tissue (autofluorescence observation) or to obtain a fluorescent light image by locally injecting a reagent such as indocyanine green (ICG) into a body tissue and emitting excitation light corresponding to a fluorescent light wavelength of the reagent upon the body tissue. The light source apparatus 11203 can be configured to be capable of supplying such narrow band light and/or excitation light corresponding to special light observation.

Figure 26:
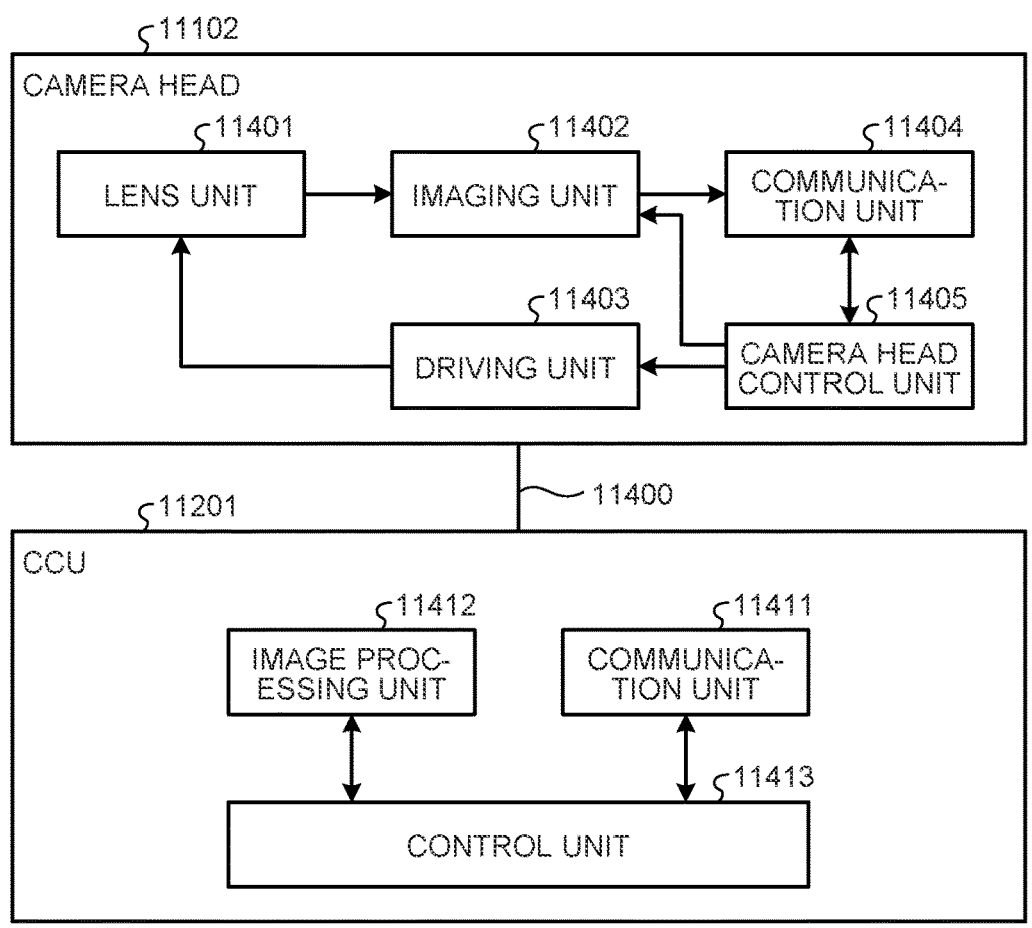
FIG. 26 is a block diagram illustrating an example of functional configurations of a camera head and a CCU.

FIG. 26 is a block diagram illustrating an example of a functional configuration of the camera head 11102 and the CCU 11201 illustrated in FIG. 24.

The camera head 11102 includes a lens unit 11401, an imaging unit 11402, a driving unit 11403, a communication unit 11404, and a camera head control unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided at a connection to the lens barrel 11101. Observation light taken in from the distal end of the lens barrel 11101 is guided to the camera head 11102 and incident on the lens unit 11401. The lens unit 11401 includes a combination of a plurality of lenses including a zoom lens and a focusing lens.

The imaging element constitutes the imaging unit 11402, and the number of imaging elements may be one (single-plate type) or a plural number (multi-plate type). When the imaging unit 11402 is of the multi-plate type, for example, image signals corresponding to respective R, G and B are generated by the imaging elements, and the image signals may be synthesized to obtain a color image. Alternatively, the imaging unit 11402 may also be configured to have a pair of imaging elements for acquiring respective image signals for the right eye and the left eye corresponding to three dimensional (3D) display. When 3D display is performed, the depth of a living body tissue in a surgical region can be figured out more accurately by the surgeon 11131. Note that when the imaging unit 11402 is of the multi-plate type, the lens units 11401 can be provided for a plurality of systems corresponding to the respective imaging elements.

Further, the imaging unit 11402 may not necessarily be provided on the camera head 11102. For example, the imaging unit 11402 may be provided immediately behind the objective lens in the lens barrel 11101.

The driving unit 11403 includes an actuator and moves the zoom lens and the focusing lens of the lens unit 11401 by a predetermined distance along an optical axis under the control of the camera head control unit 11405. Thus, the magnification and the focal point of the captured image by the imaging unit 11402 can be adjusted appropriately.

The communication unit 11404 includes a communication apparatus for transmitting and receiving various kinds of information to and from the CCU 11201. The communication unit 11404 transmits an image signal obtained from the imaging unit 11402 as RAW data to the CCU 11201 through the transmission cable 11400.

Further, the communication unit 11404 receives a control signal for controlling driving of the camera head 11102 from the CCU 11201 and supplies the control signal to the camera head control unit 11405. The control signal includes information relating to imaging conditions such as, for example, information that a frame rate of a captured image is designated, information that an exposure value upon imaging is designated and/or information that a magnification and a focal point of a captured image are designated.

Note that the imaging conditions such as the frame rate, exposure value, magnification or focal point described above may be appropriately designated by the user or may be set automatically by the control unit 11413 of the CCU 11201 on the basis of an acquired image signal. In the latter case, what is known as an auto exposure (AE) function, an auto focus (AF) function, and an auto white balance (AWB) function are mounted in the endoscope 11100.

The camera head control unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processing for an image signal in the form of RAW data transmitted from the camera head 11102.

The control unit 11413 performs various kinds of control relating to imaging of a surgical region or the like by the endoscope 11100 and display of a captured image obtained by imaging of the surgical region or the like. For example, the control unit 11413 generates a control signal for controlling driving of the camera head 11102.

Further, the control unit 11413 causes, on the basis of an image signal for which image processing has been performed by the image processing unit 11412, the display apparatus 11202 to display a captured image showing the surgical region or the like. At this time, the control unit 11413 may recognize various objects in the captured image using various image recognition technologies. For example, the control unit 11413 can recognize a surgical tool such as forceps, a particular living body region, bleeding, mist when the energy treatment tool 11112 is used and the like by detecting the shape, color and the like of edges of objects included in a captured image. The control unit 11413 may cause, when causing the display apparatus 11202 to display a captured image, various kinds of surgery supporting information to be superimposed and displayed on the image of the surgical region using a result of the recognition. When surgery supporting information is superimposed and displayed and presented to the surgeon 11131, the burden on the surgeon 11131 can be reduced and the surgeon 11131 can proceed with the surgery with certainty.

The transmission cable 11400 that connects the camera head 11102 and the CCU 11201 is an electric signal cable corresponding to communication of an electric signal, an optical fiber corresponding to optical communication, or a composite cable thereof.

Here, while, in the illustrated example, communication is performed by wire using the transmission cable 11400, the communication between the camera head 11102 and the CCU 11201 may be performed wirelessly.

Hereinabove, an example of an endoscopic surgery system to which the technology according to the present disclosure can be applied has been described. The technology according to the present disclosure can be applied to, of the configurations described above, the imaging unit 11402. Specifically, the light receiving element 10 can be applied as a part of the configuration of the imaging unit 11402. By applying the technology according to the present disclosure as a part of the configuration of the imaging unit 11402, the distance to the surgical region can be measured with high accuracy and a clearer surgical region image can be obtained.

Note that, although the endoscopic surgery system has been described as an example herein, the technology according to the present disclosure may also be applied to others, for example, a microscope surgery system, and the like.

12. APPLICATION EXAMPLE TO MOBILE BODY

The technology according to the present disclosure (the present technology) can be applied to various products. For example, the technology according to the present disclosure can be implemented as apparatuses mounted on any type of mobile bodies such as automobiles, electric vehicles, hybrid electric vehicles, motorcycles, bicycles, personal mobilities, airplanes, drones, ships, and robots.

Figure 27:
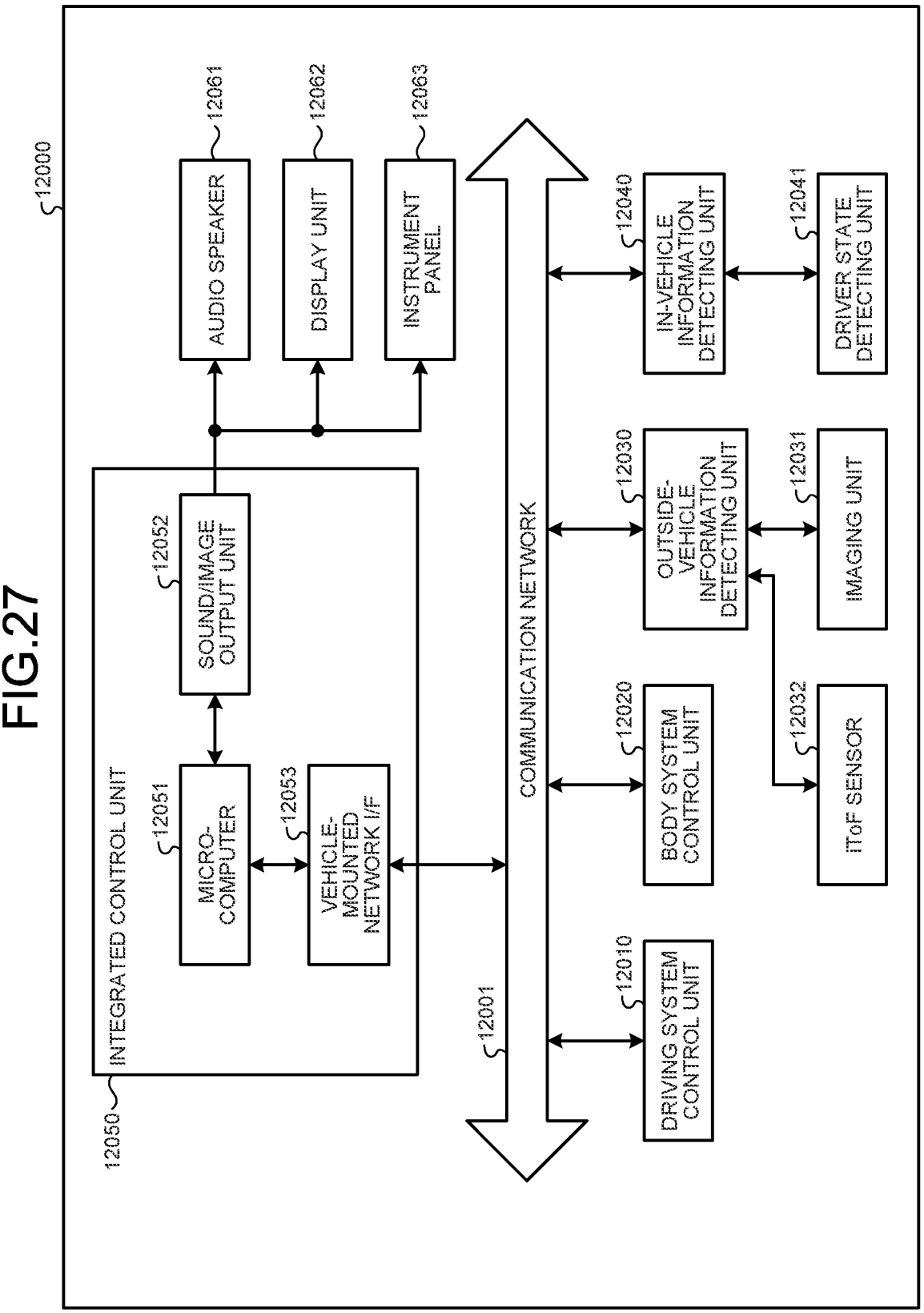
FIG. 27 is a block diagram illustrating an example of a schematic configuration of a vehicle control system.

FIG. 27 is a block diagram illustrating a schematic configuration example of a vehicle control system, which is an example of a mobile body control system to which the technology according to the present disclosure can be applied.

A vehicle control system 12000 includes a plurality of electronic control units connected to each other via a communication network 12001. In the example illustrated in FIG. 27, the vehicle control system 12000 includes a driving system control unit 12010, a body system control unit 12020, an outside-vehicle information detecting unit 12030, an in-vehicle information detecting unit 12040, and an integrated control unit 12050. Further, a microcomputer 12051, a sound/image output unit 12052, and a vehicle-mounted network interface (I/F) 12053 are illustrated as a functional configuration of the integrated control unit 12050.

The driving system control unit 12010 controls the operation of apparatuses related to the driving system of the vehicle in accordance with various kinds of programs. For example, the driving system control unit 12010 functions as a control apparatus for a driving force generating apparatus for generating the driving force of the vehicle, such as an internal combustion engine, a driving motor, or the like, a driving force transmitting mechanism for transmitting the driving force to wheels, a steering mechanism for adjusting the steering angle of the vehicle, a braking apparatus for generating the braking force of the vehicle, and the like.

The body system control unit 12020 controls the operation of various kinds of apparatuses provided to a vehicle body in accordance with various kinds of programs. For example, the body system control unit 12020 functions as a control apparatus for a keyless entry system, a smart key system, a power window apparatus, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock apparatus, the power window apparatus, the lamps, or the like of the vehicle.

The outside-vehicle information detecting unit 12030 detects information of the outside of the vehicle including the vehicle control system 12000. For example, the outside-vehicle information detecting unit 12030 is connected with an imaging unit 12031. The outside-vehicle information detecting unit 12030 causes the imaging unit 12031 to capture an image of the outside of the vehicle, and receives the captured image. On the basis of the received image, the outside-vehicle information detecting unit 12030 may perform processing of detecting an object such as a human, a car, an obstacle, a sign, a character on a road surface, or the like, or processing of detecting a distance. Further, an iToF sensor 12032 is connected to the outside-vehicle information detecting unit 12030. The iToF sensor 12032 can function as the distance measurement module 1 according to the embodiment of the present disclosure.

The imaging unit 12031 is an optical sensor that receives light and outputs an electric signal corresponding to the received light amount of the light. The imaging unit 12031 can output the electric signal as an image or can output the electric signal as information of distance measurement. Further, the light received by the imaging unit 12031 may be visible light, or may be invisible light such as infrared rays or the like.

The in-vehicle information detecting unit 12040 detects information of the inside of the vehicle. The in-vehicle information detecting unit 12040 is, for example, connected with a driver state detecting unit 12041 that detects the state of a driver. The driver state detecting unit 12041 includes, for example, a camera that images the driver, and on the basis of detection information input from the driver state detecting unit 12041, the in-vehicle information detecting unit 12040 may calculate a degree of fatigue or degree of concentration of the driver, or may determine whether the driver is dozing.

The microcomputer 12051 can calculate a control target value for the driving force generating apparatus, the steering mechanism, or the braking apparatus on the basis of the inside- and outside-vehicle information acquired by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) including collision avoidance or shock mitigation for the vehicle, following driving based on a following distance, vehicle speed maintaining driving, a warning of collision of the vehicle, a warning of deviation of the vehicle from a lane, or the like.

Further, the microcomputer 12051 can perform cooperative control intended for automatic driving, which causes the vehicle to travel autonomously without depending on the operation of the driver, or the like, by controlling the driving force generating apparatus, the steering mechanism, the braking apparatus, or the like on the basis of the information around the vehicle acquired by the outside-vehicle information detecting unit 12030 or the in-vehicle information detecting unit 12040.

Further, the microcomputer 12051 can output a control command to the body system control unit 12030 on the basis of the outside-vehicle information acquired by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output unit 12052 transmits an output signal of at least one of a sound or an image to an output apparatus capable of visually or auditorily notifying an occupant of the vehicle or the outside of the vehicle of information. In the example of FIG. 27, an audio speaker 12061, a display unit 12062, and an instrument panel 12063 are illustrated as the output apparatus. The display unit 12062 may, for example, include at least one of an on-board display or a head-up display.

Figure 28:
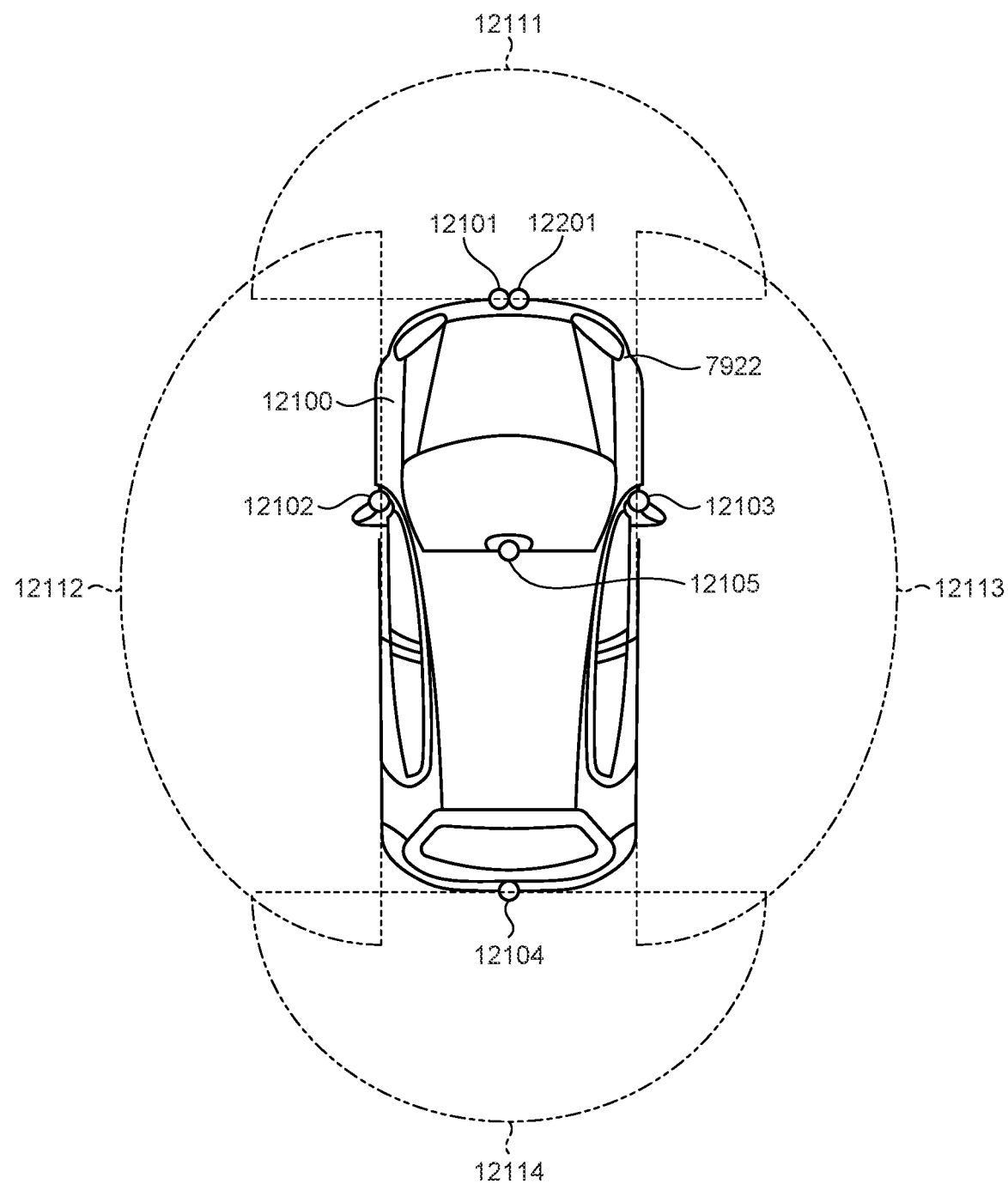
FIG. 28 is an explanatory diagram illustrating an example of installation positions of an outside-vehicle information detecting unit and an imaging unit.

FIG. 28 is a diagram illustrating an example of the installation position of the imaging unit 12031.

In FIG. 28, imaging units 12101, 12102, 12103, 12104, and 12105 are provided as the imaging unit 12031.

The imaging units 12101, 12102, 12103, 12104, and 12105 are, for example, disposed at positions on a front nose, sideview mirrors, a rear bumper, and a back door of a vehicle 12100 as well as a position on an upper portion of a windshield within the interior of the vehicle. The imaging unit 12101 provided on the front nose and the imaging unit 12105 provided on the upper portion of the windshield within the interior of the vehicle mainly acquire an image of the front of the vehicle 12100. The imaging units 12102 and 12103 provided on the sideview mirrors mainly acquire an image of the sides of the vehicle 12100. The imaging unit 12104 provided on the rear bumper or the back door mainly acquires an image of the rear of the vehicle 12100. The imaging unit 12105 provided on the upper portion of the windshield within the interior of the vehicle is used mainly to detect a preceding vehicle, a pedestrian, an obstacle, a signal, a traffic sign, a lane, or the like. Further, an iToF sensor module 12201 in which the irradiation unit 20 and the light receiving unit 30 of the distance measurement module 1 according to the embodiment of the present disclosure are incorporated is provided, for example, at the front nose of the vehicle 12100.

Note that FIG. 24 illustrates an example of imaging ranges of the imaging units 12101 to 12104. An imaging range 12111 indicates the imaging range of the imaging unit 12101 provided on the front nose, imaging ranges 12112 and 12113 respectively indicate the imaging ranges of the imaging units 12102 and 12103 provided on the sideview mirrors, and an imaging range 12114 indicates the imaging range of the imaging unit 12104 provided on the rear bumper or the back door. A bird's-eye image of the vehicle 12100 as viewed from above is obtained by superimposing image data imaged by the imaging units 12101 to 12104, for example.

At least one of the imaging units 12101 to 12104 may have a function of acquiring the distance information. For example, at least one of the imaging units 12101 to 12104 may be a stereo camera including a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging units 12101 to 12104, and thereby extract, as a preceding vehicle, the nearest three-dimensional object particularly that is present on a traveling path of the vehicle 12100 and travels in substantially the same direction as the vehicle 12100 at a predetermined speed (for example, equal to or more than 0 km/h). Furthermore, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that causes the vehicle to travel autonomously without depending on the operation of the driver or the like.

For example, the microcomputer 12051 can classify three-dimensional object data regarding three-dimensional objects into a two-wheeled vehicle, a standard-sized vehicle, a large-sized vehicle, a pedestrian, a utility pole, and other three-dimensional objects on the basis of the distance information obtained from the imaging units 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle, and in a situation in which the collision risk is equal to or higher than a set value and there is a possibility of collision, the microcomputer 12051 outputs a warning to the driver via the audio speaker 12061 or the display unit 12062, and performs forced deceleration or avoidance steering via the driving system control unit 12010, thereby enabling assist in driving to avoid collision.

At least one of the imaging units 12101 to 12104 may be an infrared camera that detects infrared rays. The microcomputer 12051 can, for example, recognize a pedestrian by determining whether or not there is a pedestrian in captured images of the imaging units 12101 to 12104. Such recognition of a pedestrian is, for example, performed by a procedure of extracting characteristic points in the captured images of the imaging units 12101 to 12104, which are infrared cameras, and a procedure of determining whether or not it is the pedestrian by performing pattern matching processing on a series of characteristic points representing the contour of the object. When the microcomputer 12051 determines that there is a pedestrian in the captured images of the imaging units 12101 to 12104, and thus recognizes the pedestrian, the sound/image output unit 12052 controls the display unit 12062 so that a square contour line for emphasis is displayed so as to be superimposed on the recognized pedestrian. Further, the sound/image output unit 12052 may control the display unit 12062 so that an icon or the like indicating the pedestrian is displayed at a desired position.

Hereinabove, an example of the vehicle control system to which the technology according to the present disclosure can be applied is described. The technology according to the present disclosure can be applied to, of the configuration described above, the outside-vehicle information detecting unit 12030 and the imaging unit 12031. Specifically, the light receiving element 10 or the distance measurement module 1 can be applied to a distance detection processing block of the outside-vehicle information detecting unit 12030 and the imaging unit 12031. By applying the technology according to the present disclosure to the outside-vehicle information detecting unit 12030 and the imaging unit 12031, the distance to an object such as a person, a car, an obstacle, a sign, or a character on a road surface can be measured with high accuracy, and the fatigue of the driver can be reduced or the safety of the driver or the vehicle can be enhanced using the obtained distance information.

13. SUPPLEMENT

While the preferred embodiments of the present disclosure have been described in detail above with reference to the accompanying drawings, the technical scope of the present disclosure is not limited to or by such examples. It will be apparent to those skilled in the art of the present disclosure that various modifications and alterations can be conceived within the scope of the technical idea described in the claims and naturally fall within the technical scope of the present disclosure.

Further, the effects described in the present specification are merely illustrative or exemplary and are not limited. That is, the technology according to the present disclosure can have other effects apparent to those skilled in the art from the description of the present specification, in addition to or instead of the above effects.

Note that the present technology can also have the following configurations.

(1)

A light receiving element comprising:
- a photoelectric conversion unit that is provided in a semiconductor substrate and converts light into a charge;
- a first charge accumulation unit to which the charge is transferred from the photoelectric conversion unit;
- a second charge accumulation unit to which the charge is transferred from the photoelectric conversion unit,
- wherein
- each of the first and second charge accumulation units includes a stack of an electrode, a first insulating layer, and a semiconductor layer.

(2)

The light receiving element according to (1), wherein each of the first and second charge accumulation units accumulates the charge in an inversion region generated on an outermost surface of the semiconductor layer located immediately below the first insulating layer by applying a first voltage to the electrode.

(3)

The light receiving element according to (1), wherein the stack further includes an embedded layer embedded in the semiconductor layer between the first insulating layer and the semiconductor layer.

(4)

The light receiving element according to (3), wherein
the semiconductor layer is a semiconductor layer of a first conductivity type, and
the embedded layer is a semiconductor layer of a second conductivity type that is a conductivity type opposite to the first conductivity type.

(5)

The light receiving element according to (3) or (4), wherein each of the first and second charge accumulation units accumulates the charge in a channel region generated in the semiconductor layer by applying a second voltage to the electrode.

(6)

A light receiving element comprising:
- a photoelectric conversion unit that is provided in a semiconductor substrate and converts light into a charge;
- a first charge accumulation unit to which the charge is transferred from the photoelectric conversion unit;
- a second charge accumulation unit to which the charge is transferred from the photoelectric conversion unit,
- wherein
- each of the first and second charge accumulation units includes:
- a semiconductor layer;
- an insulating layer embedded in a trench formed in the semiconductor layer; and
- a vertical electrode embedded in the insulating layer.

(7)

The light receiving element according to any one of (1) to (5), wherein
the electrode is made of a metal film, and
the first insulating layer is made of an oxide film.

(8)

The light receiving element according to (7), wherein the oxide film has a film thickness of 5.0 nm or less.

(9)

The light receiving element according to any one of (1) to (5), wherein the first insulating layer has a relative dielectric constant of 4 or more.

(10)

The light receiving element according to any one of (1) to (5), further comprising:
- a first sorting transistor that sorts the charge from the photoelectric conversion unit to the first charge accumulation unit; and
- a second sorting transistor that sorts the charge from the photoelectric conversion unit to the second charge accumulation unit.

(11)

The light receiving element according to (10), wherein a predetermined voltage is applied to each of gates of the first and second sorting transistors at different timings.

(12)

The light receiving element according to any one of (1) to (11), further comprising:
- a moth-eye structure that is provided on a surface opposite to a front surface of the semiconductor substrate and formed with fine unevenness.

(13)

The light receiving element according to any one of (1) to (11), further comprising:
- a first pixel isolation portion penetrating the semiconductor substrate.

(14)

The light receiving element according to any one of (1) to (11), further comprising:
- a second pixel isolation portion penetrating from a surface opposite to a front surface of the semiconductor substrate to a middle of the semiconductor substrate along a thickness direction of the semiconductor substrate.

(15)

The light receiving element according to (10), further comprising:
- one or more floating diffusion regions;

a first transfer transistor that transfers the charge transferred to the first charge accumulation unit to the one or more floating diffusion regions; and
a second transfer transistor that transfers the charge transferred to the second charge accumulation unit to the one or more floating diffusion regions.

(16)
The light receiving element according to (15), further comprising:
one or more amplification transistors that amplify the charge transferred to the floating diffusion region and output the amplified charge as a pixel signal;
one or more selection transistors that output the pixel signal according to a selection signal; and
one or more reset transistors that reset the charge accumulated in the floating diffusion region.

(17)
The light receiving element according to (16), wherein
the first insulating layer is made of a first oxide film,
each of the first and second transfer transistors includes a second oxide film provided on the semiconductor substrate, and
the first oxide film has a film thickness thinner than a film thickness of the second oxide film.

(18)
The light receiving element according to (17), wherein
each of the amplification transistor, the selection transistor, and the reset transistor includes a third oxide film provided on the semiconductor substrate, and
the third oxide film of the amplification transistor has a film thickness thinner than a film thickness of the third oxide films of the selection transistor and the reset transistor.

(19)
The light receiving element according to (16), wherein
each of the first and second transfer transistors includes a second insulating layer provided on the semiconductor substrate, and
the first insulating layer has a relative dielectric constant higher than a relative dielectric constant of the second insulating layer.

(20)
The light receiving element according to (19), wherein
each of the amplification transistor, the selection transistor, and the reset transistor includes a third insulating layer provided on the semiconductor substrate, and
the third insulating layer of the amplification transistor has a relative dielectric constant higher than a relative dielectric constant of the third insulating layers of the selection transistor and the reset transistor.

(21)
The light receiving element according to (1), further comprising:
a plurality of third charge accumulation units to which the charge is transferred from the photoelectric conversion unit,
wherein
each of the third charge accumulation units includes a stack of an electrode, a fourth insulating layer, and a semiconductor layer.

(22)
A light receiving apparatus comprising one or more light receiving elements, the light receiving element including:
a photoelectric conversion unit that is provided in a semiconductor substrate and converts light into a charge;
a first charge accumulation unit to which the charge is transferred from the photoelectric conversion unit;
a second charge accumulation unit to which the charge is transferred from the photoelectric conversion unit,
wherein
each of the first and second charge accumulation units includes a stack of an electrode, a first insulating layer, and a semiconductor layer.

(23)
The light receiving apparatus according to (22), further comprising:
an irradiation unit that irradiates an object with light while periodically changing brightness; and
an irradiation control unit that controls the irradiation unit,
wherein
the photoelectric conversion unit receives reflected light from the object.

REFERENCE SIGNS LIST

1 DISTANCE MEASUREMENT MODULE
10 LIGHT RECEIVING ELEMENT
12 PIXEL ARRAY UNIT
20 IRRADIATION UNIT
30 LIGHT RECEIVING UNIT
32 VERTICAL DRIVE CIRCUIT UNIT
34 COLUMN SIGNAL PROCESSING CIRCUIT UNIT
36 HORIZONTAL DRIVE CIRCUIT UNIT
38 OUTPUT CIRCUIT UNIT
40 CONTROL UNIT
42 PIXEL DRIVE WIRING
44 CONTROL CIRCUIT UNIT
46 HORIZONTAL SIGNAL LINE
48 VERTICAL SIGNAL LINE
50 SORTING TRANSISTOR DRIVE UNIT
52 SIGNAL PROCESSING UNIT
54 DATA STORAGE UNIT
60 PROCESSING UNIT
100, 102, 102a, 102b, 104a, 104b, 106a, 106b, 108a, 108b, 110a, 110b, 112a, 112b, 114a, 114b, 116a, 116b N-TYPE SEMICONDUCTOR REGION
150a, 150b, 152a, 152b, 156a, 156b, 158a, 158b, 160a, 160b, 162a, 162b GATE ELECTRODE
154a, 154b, 306, 406 ELECTRODE
170 INSULATING LAYER
172 EMBEDDED LAYER
174 TRENCH
178 EMBEDDED ELECTRODE PORTION
200 SEMICONDUCTOR SUBSTRATE
202 ANTIREFLECTION FILM
202a MOTH-EYE STRUCTURE
204 PLANARIZATION FILM
206 LIGHT SHIELDING FILM
208 ON-CHIP LENS
210, 210a PIXEL ISOLATION PORTION
300 WIRING LAYER
302, 402 INSULATING FILM
304, 404 METAL FILM
400 SUBSTRATE
600, 602 CENTER LINE
710 VIA
720, 720a INSULATING FILM
730 SIDEWALL
740 HIGH DIELECTRIC CONSTANT FILM
800 OBJECT
802a, 802b REGION

900 SMARTPHONE
901 CPU
902 ROM
903 RAM
904 STORAGE APPARATUS
905 COMMUNICATION MODULE
907 SENSOR MODULE
908 DISTANCE MEASUREMENT MODULE
909 IMAGING APPARATUS
910 DISPLAY APPARATUS
911 SPEAKER
912 MICROPHONE
913 INPUT APPARATUS
AMP, AMP1, AMP2 AMPLIFICATION TRANSISTOR
FD, FD1, FD2 FLOATING DIFFUSION REGION
MEM, MEM1, MEM2 CHARGE ACCUMULATION UNIT
O CENTER POINT
OFG, OFG1, OFG2 CHARGE DISCHARGE TRANSISTOR
PD PHOTODIODE
RST, RST1, RST2 RESET TRANSISTOR
SEL, SEL1, SEL2 SELECTION TRANSISTOR
TG, TG1, TG2 TRANSFER TRANSISTOR
VDD POWER SUPPLY POTENTIAL
VG, VG1, VG2 SORTING TRANSISTOR
VSL, VSL1, VSL2 SIGNAL LINE

What is claimed is:

1. A light receiving element, comprising:
   a photoelectric conversion unit that is provided in a semiconductor substrate and converts light into a charge;
   a first charge accumulation unit to which the charge is transferred from the photoelectric conversion unit;
   a second charge accumulation unit to which the charge is transferred from the photoelectric conversion unit;
   a first transfer transistor that transfers the charge transferred to the first charge accumulation unit; and
   a second transfer transistor that transfers the charge transferred to the second charge accumulation unit,
   wherein each of the first and second charge accumulation units includes a stack of an electrode, a first insulating layer, and a semiconductor layer,
   wherein the first insulating layer is made of a first oxide film,
   wherein each of the first transfer transistor and the second transfer transistor includes a second oxide film provided on the semiconductor substrate, and
   wherein the first oxide film has a film thickness thinner than a film thickness of the second oxide film.

2. The light receiving element according to claim 1, wherein each of the first and second charge accumulation units accumulates the charge in an inversion region generated on an outermost surface of the semiconductor layer located immediately below the first insulating layer by applying a first voltage to the electrode.

3. The light receiving element according to claim 1, wherein the stack further includes an embedded layer embedded in the semiconductor layer between the first insulating layer and the semiconductor layer.

4. The light receiving element according to claim 3, wherein
   the semiconductor layer is a semiconductor layer of a first conductivity type, and
   the embedded layer is a semiconductor layer of a second conductivity type that is a conductivity type opposite to the first conductivity type.

5. The light receiving element according to claim 3, wherein each of the first and second charge accumulation units accumulates the charge in a channel region generated in the semiconductor layer by applying a second voltage to the electrode.

6. The light receiving element according to claim 1, wherein the electrode is made of a metal film.

7. The light receiving element according to claim 6, wherein the first oxide film has a film thickness of 5.0 nm or less.

8. The light receiving element according to claim 1, wherein the first insulating layer has a relative dielectric constant of 4 or more.

9. The light receiving element according to claim 1, further comprising:
   a first sorting transistor that sorts the charge from the photoelectric conversion unit to the first charge accumulation unit; and
   a second sorting transistor that sorts the charge from the photoelectric conversion unit to the second charge accumulation unit.

10. The light receiving element according to claim 9, wherein a predetermined voltage is applied to each gate of the first sorting transistor and the second sorting transistor at different times.

11. The light receiving element according to claim 9, further comprising:
    one or more floating diffusion regions,
    wherein the first transfer transistor transfers the charge transferred to the first charge accumulation unit to the one or more floating diffusion regions, and
    wherein the second transfer transistor transfers the charge transferred to the second charge accumulation unit to the one or more floating diffusion regions.

12. The light receiving element according to claim 11, further comprising:
    one or more amplification transistors that amplify the charge transferred to the one or more floating diffusion regions and output the amplified charge as a pixel signal;
    one or more selection transistors that output the pixel signal according to a selection signal; and
    one or more reset transistors that reset the charge accumulated in the one or more floating diffusion regions.

13. The light receiving element according to claim 12, wherein
    each of the one or more amplification transistors, the one or more selection transistors, and the one or more reset transistors includes a third oxide film provided on the semiconductor substrate, and
    the third oxide film of the one or more amplification transistors has a film thickness thinner than a film thickness of the third oxide films of the one or more selection transistors and the one or more reset transistors.

14. The light receiving element according to claim 12, wherein each of the first transfer transistor and the second transfer transistor includes a second insulating layer provided on the semiconductor substrate, and
    the first insulating layer has a relative dielectric constant higher than a relative dielectric constant of the second insulating layer.

15. The light receiving element according to claim 14, wherein
    each of the one or more amplification transistors, the one or more selection transistors, and the one or more reset transistors includes a third insulating layer provided on the semiconductor substrate, and the third insulating layer of the one or more amplification transistors has a relative dielectric constant higher than a relative dielectric constant of the third insulating layer of the one or more selection transistors and a relative dielectric constant higher than a relative dielectric constant of the third insulating layer of the one or more reset transistors.

16. The light receiving element according to claim 1, further comprising: a moth-eye structure that is provided on a surface opposite to a front surface of the semiconductor substrate and formed with fine unevenness.

17. The light receiving element according to claim 1, further comprising: a first pixel isolation portion penetrating the semiconductor substrate.

18. The light receiving element according to claim 17, further comprising: a second pixel isolation portion penetrating from a surface opposite to a front surface of the semiconductor substrate to a middle portion of the semiconductor substrate along a thickness direction of the semiconductor substrate.

19. The light receiving element according to claim 1, further comprising:
   a plurality of third charge accumulation units to which the charge is transferred from the photoelectric conversion unit,
   wherein each third charge accumulation unit of the plurality of third charge accumulation units includes a stack of a second electrode, a fourth insulating layer, and a second semiconductor layer.

20. A light receiving element, comprising:
   a photoelectric conversion unit that is provided in a semiconductor substrate and converts light into a charge;
   a first charge accumulation unit to which the charge is transferred from the photoelectric conversion unit;
   a second charge accumulation unit to which the charge is transferred from the photoelectric conversion unit,
   wherein each of the first and second charge accumulation units includes:
      a semiconductor layer;
      a first insulating layer embedded in a trench formed in the semiconductor layer; and
      a vertical electrode embedded in the first insulating layer;
   a first transfer transistor that transfers the charge transferred to the first charge accumulation unit; and
   a second transfer transistor that transfers the charge transferred to the second charge accumulation unit,
   wherein each of the first transfer transistor and the second transfer transistor includes a second insulating layer provided on the semiconductor substrate, and
   wherein the first insulating layer has a relative dielectric constant higher than a relative dielectric constant of the second insulating layer.

21. A light receiving apparatus comprising one or more light receiving elements, the light receiving element including:
   a photoelectric conversion unit that is provided in a semiconductor substrate and converts light into a charge;
   a first charge accumulation unit to which the charge is transferred from the photoelectric conversion unit;
   a second charge accumulation unit to which the charge is transferred from the photoelectric conversion unit;
   a first transfer transistor that transfers the charge transferred to the first charge accumulation unit; and
   a second transfer transistor that transfers the charge transferred to the second charge accumulation unit,
   wherein each of the first and second charge accumulation units includes a stack of an electrode, a first insulating layer, and a semiconductor layer,
   wherein the first insulating layer is made of a first oxide film,
   wherein each of the first transfer transistor and the second transfer transistor includes a second oxide film provided on the semiconductor substrate, and
   wherein the first oxide film has a film thickness thinner than a film thickness of the second oxide film.

22. The light receiving apparatus according to claim 21, further comprising:
   an irradiation unit that irradiates an object with light while periodically changing brightness; and
   an irradiation control unit that controls the irradiation unit,
   wherein the photoelectric conversion unit receives reflected light from the object.

* * * * *